US008623855B2

(12) United States Patent
Bai et al.

(10) Patent No.: US 8,623,855 B2
(45) Date of Patent: Jan. 7, 2014

(54) AZETIDINONE COMPOUNDS AND MEDICAL USE THEREOF

(75) Inventors: Hua Bai, Zhejiang (CN); Xuyang Zhao, Sichuan (CN); Xiaojie Xu, Zhejiang (CN); Xiaoyu Liu, Zhejiang (CN); Yuncai Zhang, Zhejiang (CN); Ying Chen, Sichuan (CN); Xiaohe Zheng, Zhejiang (CN); Maojian Gu, Shanghai (CN); Qifeng Zhu, Zhejiang (CN); Yong Zhang, Zhejiang (CN); Hairong Luo, Zhejiang (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 13/389,932

(22) PCT Filed: Aug. 9, 2010

(86) PCT No.: PCT/CN2010/001206
§ 371 (c)(1),
(2), (4) Date: Apr. 20, 2012

(87) PCT Pub. No.: WO2011/017907
PCT Pub. Date: Feb. 17, 2011

(65) Prior Publication Data
US 2012/0208994 A1 Aug. 16, 2012

(30) Foreign Application Priority Data
Aug. 11, 2009 (CN) .......................... 2009 1 0162888

(51) Int. Cl.
A01N 43/00 (2006.01)
C07D 205/00 (2006.01)

(52) U.S. Cl.
USPC ..................................... 514/210.02; 540/200

(58) Field of Classification Search
USPC ....................................................... 540/200
See application file for complete search history.

(56) References Cited

U.S. PATENT DOCUMENTS

| 5,627,176 | A | 5/1997 | Kirkup et al. |
| 5,698,548 | A | 12/1997 | Dugar et al. |
| 5,756,470 | A | 5/1998 | Yumibe et al. |
| 5,767,115 | A | 6/1998 | Rosenblum et al. |
| 5,846,966 | A | 12/1998 | Rosenblum et al. |
| RE37,721 | E | 5/2002 | Rosenblum et al. |

FOREIGN PATENT DOCUMENTS

| CN | 1144522 A | 3/1997 |
| EP | 0524595 A1 | 1/1993 |
| WO | 9302048 A1 | 2/1993 |
| WO | 9417038 A1 | 8/1994 |
| WO | 9508532 A1 | 3/1995 |
| WO | 9526334 A1 | 10/1995 |
| WO | 9535277 A1 | 12/1995 |
| WO | 9616037 A1 | 5/1996 |
| WO | 9619450 A1 | 6/1996 |
| WO | 9716455 A1 | 5/1997 |
| WO | 0250027 A1 | 6/2002 |
| WO | 0250060 A1 | 6/2002 |
| WO | 0250068 A1 | 6/2002 |
| WO | 0250090 A1 | 6/2002 |
| WO | 02066464 A1 | 8/2002 |
| WO | 04000803 A1 | 12/2003 |
| WO | 04000804 A1 | 12/2003 |
| WO | 04000805 A1 | 12/2003 |

OTHER PUBLICATIONS

Chen, Lian-Yong. J. Org. Chem. 1996, 61, 8341-8343.*
International Search Report and Written Opinion, PCT/CN2010/001206, dated Nov. 18, 2010.
Extended European Search Report for Application No. EP10807852 dated Mar. 14, 2013.

* cited by examiner

*Primary Examiner* — Noble Jarrell
*Assistant Examiner* — Laura Daniel
(74) *Attorney, Agent, or Firm* — Lerner, David, Littenberg, Krumholz & Mentlik, LLP

(57) ABSTRACT

Preparation of azetidinone compounds and medical use thereof are provided by the present invention. More particularly, azetidionne compounds, shown as formula (I), wherein $R^1$, $R^2$, $R^3$, $R^4$, $R^5$ and $R^6$ are defined in description, and preparation methods thereof are provided by the present invention. The compounds of the present invention can reduce the levels of total cholesterol (TC) and low density lipoprotein cholesterol (LDL-C) in plasma, and can be used as medicaments for reducing cholesterol in blood. Therefore the compounds of the present invention can be used to treat or prevent diseases of atherosclerosis, cacergasia of blood vessel, cardiac failure, coronary artery disease, angiocardiopathy, myocardial, angina, hyperlipoidemia and hypercholesteremia and the like. Preparation method of compounds of formula (I) and intermediate compounds are also provided by the present invention.

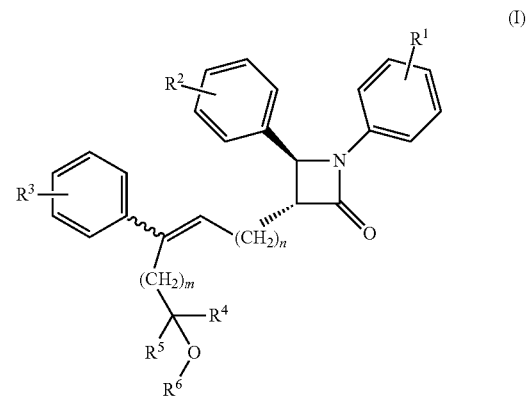

26 Claims, No Drawings

AZETIDINONE COMPOUNDS AND MEDICAL USE THEREOF

CROSS-REFERENCE TO RELATED APPLICATIONS

This application is a national phase entry under 35 U.S.C. §371 of International Application No. PCT/CN2010/001206, filed Aug. 9, 2010, published in Chinese, which claims the benefit of the filing date of Chinese Patent Application No. 200910162888.8, filed Aug. 11, 2009, the entire disclosure of which is hereby incorporated herein by reference.

FIELD OF THE INVENTION

The present invention relates to new azetidinone compounds as a serum cholesterol reducing agent, and treatment of diseases by administering the acetidinone compounds. The present invention also relates to processes for preparation of the azetidinone compounds.

BACKGROUND OF THE INVENTION

Atherosclerotic coronary artery disease is a major cause of death and morbidity as well as a significant drain on healthcare resources in the western world. It is well known that cholesteryl esters are a major risk factor for atherosclerotic lesions, and also a major storage form in the arterial wall cells of the cholesterol.

Regulations of cholesterol homeostasis of human and animal bodies involve regulations of dietary cholesterol and regulations of biosynthesis of cholesterol, biosynthesis of bile acid and metabolism of plasma lipoprotein containing cholesterol. The cholesterol from food and bile origin is absorbed from the intestine, and enters the circulation as a component of chylomicrons. In another aspect, the cholesterol is biosynesized and metabolized by the liver, and therefore, it is the major determinant of plasma cholesterol levels. The liver is the site for synthesis and secretion of the very low density lipoprotein (VLDL), and then the VLDL is metabolized to the low density lipoprotein (LDL) in circulation. LDL is a major form of cholesterol with lipoprotein in plasma, and its increased concentration associates with the increase of atherosclerosis. No matter by what means, if the intestinal cholesterol absorption is reduced, less cholesterol will be delivered to the liver, which results in a reduction in the production of hepatic lipoprotein (VLDL), as well as an increase in hepatic clearance of plasma cholesterol.

At present, many clinical studies have clearly demonstrated that increase of the total serum cholesterol level is one of the major risk factors for coronary artery disease. The higher the level of the total serum cholesterol is, the greater the risk is and the earlier the time is for the occurrence of the atherosclerosis. The total serum cholesterol is reduced by 1%, the risk of the occurrence of coronary artery disease can be reduced by 2%. Therefore, inhibition of the formation of cholesteryl esters and reduction of the serum cholesterol may inhibit the development of formation of atherosclerotic lesions, reduce the accumulation of cholesteryl esters in arterial walls and prevent the intestinal absorption of dietary cholesterol.

Even with the current diverse range of therapeutic agents, such as statins, e.g. simvastatin and fluvastatin, bile acid binder, fibrates, niacin analogues, significant proportion of the hypercholesterolaemic population is unable to reach target cholesterol levels, or drug interactions or drug safety preclude the long term use needed to reach the target levels. Therefore, there is still a need to develop additional agents that are more efficacious and are better tolerated.

Compounds possessing such cholesterol absorption inhibitory activity have been described, see for instance the compounds described in WO 93/02048, WO 94/17038, WO 95/08532, WO 95/26334, WO 95/35277, WO 96/16037, WO 96/19450, WO 97/16455, WO 02/50027, WO 02/50060, WO 02/50068, WO 02/50090, WO 02/66464, WO 04/000803, WO 04/000804, WO04/000805, U.S. Pat. No. 5,756,470, U.S. Pat. No. 5,767,115, and US RE37721. Most of them reported the azetidinone compounds for reduction of cholesterol and/or inhibitory of the formation of lesions in artery walls of mammals.

The present invention is based on the above discovery of surprising inhibition of 2-azetidinone derivatives on cholesterol absorption. The present invention synthesizes and structurally modifies these azetidinone compounds, to look for azetidinone compounds with more efficacious inhibitory effect on cholesterol. The compounds of the present invention are not disclosed in any of the above applications.

The present invention further relates to the use of the azetidinone compounds of the present invention to reduce serum cholesterol levels.

SUMMARY OF THE INVENTION

One object of the present invention is to disclose new serum cholesterol lowering agents, i.e. azetidinone compounds or pharmaceutically acceptable salts thereof.

Another object of the present invention is to disclose processes of preparation of the said azetidinone compounds.

The compounds of the present invention are compounds represented by formula (I):

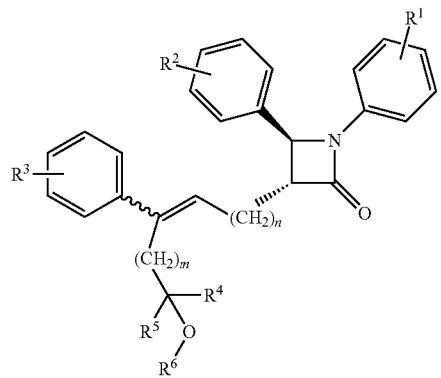

Formula (I)

or a pharmaceutically acceptable salt thereof, wherein:

$R^1$ is 1-3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, hydroxyl, $C_1$-$C_6$ alkoxy, benzyloxy and —$OCOR^7$;

$R^2$ is 1-3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, hydroxyl, $C_1$-$C_6$ alkoxy, $C_6$-$C_{10}$ aryloxy, ($C_6$-$C_{10}$ aryl) methoxy and —$OCOR^7$;

$R^3$ is 1-3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, $C_1$-$C_6$ alkoxy and benzyloxy;

$R^4$ is selected from the group consisting of hydrogen, $C_1$-$C_6$ alkyl, $C_2$-$C_6$ alkenyl and $C_3$-$C_6$ cycloalkyl;

$R^5$ is selected from the group consisting of hydrogen, $C_1$-$C_6$ alkyl, $C_2$-$C_6$ alkenyl and $C_3$-$C_6$ cycloalkyl;

$R^6$ is hydrogen or —$COR^7$;

$R^7$ is $C_1$-$C_{10}$ alkyl, phenyl or phenyl substituted by at least one substituent selected from the group consisting of halogen, trifluoromethyl, cyano, hydroxyl, $C_1$-$C_6$ alkyl, $C_2$-$C_6$ alkenyl, $C_3$-$C_6$ cycloalkyl, $C_1$-$C_6$ alkoxy, phenoxy and benzyloxy;

m is 0, 1, 2 or 3;

n is 1, 2 or 3; and the carbon-carbon double bond is Z configuration or E configuration.

In the above embodiment of the present invention, "halogen" includes fluorine, chlorine, bromine and iodine; "$C_1$-$C_6$ alkyl" includes methyl, ethyl, n-propyl, isopropyl, n-butyl, isobutyl, tert-butyl, n-pentyl, isopentyl, neopentyl, n-hexyl, isohexyl, neohexyl; "$C_2$-$C_6$ alkenyl" includes vinyl, propenyl, allyl, butenyl, pentenyl, hexenyl; "$C_3$-$C_6$ cycloalkyl" includes cyclopropyl, cyclobutyl, cyclopentyl, cyclohexyl; "$C_1$-$C_6$ alkoxy" includes methoxy, ethoxy, n-propoxy, isopropoxy, n-butoxy, isobutoxy, tert-butoxy, n-penoxy, isopenoxy, neopenoxy, n-hexoxy, isohexoxy, neohexoxy.

Another aspect of the present invention relates to intermediate compounds for preparing the compound of formula (I), a compound represented by formula (III):

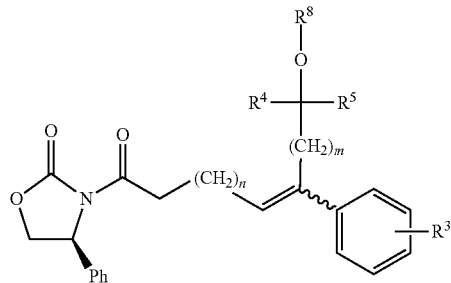

wherein:

$R^3$ is 1-3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, $C_1$-$C_6$ alkoxy and benzyloxy;

$R^4$ is selected from the group consisting of hydrogen, $C_1$-$C_6$ alkyl, $C_2$-$C_6$ alkenyl and $C_3$-$C_6$ cycloalkyl;

$R^5$ is selected from the group consisting of hydrogen, $C_1$-$C_6$ alkyl, $C_2$-$C_6$ alkenyl and $C_3$-$C_6$ cycloalkyl;

$R^8$ is a protecting group of hydroxyl, such as acetyl, tert-butyldimethylsily (TBDMS), trimethylsily (TMS), tert-butyldiphenylsily (TBDPS) or the like;

m is 0, 1, 2 or 3;

n is 1, 2 or 3; and the carboncarbon double bond is Z configuration or E configuration.

A compound represented by formula V:

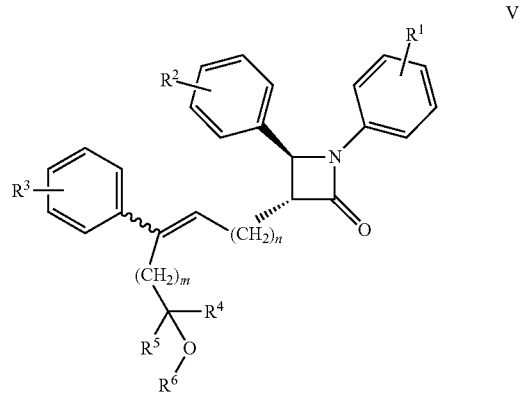

wherein, $R^1$, $R^2$, $R^3$, $R^4$, $R^5$, $R^8$, m and n are as defined above.

A compound represented by formula IV:

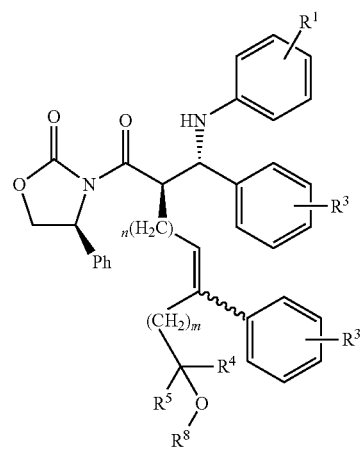

wherein, $R^1$, $R^2$, $R^3$, $R^4$, $R^5$, $R^8$, m and n are as defined above.

A compound represented by formula L:

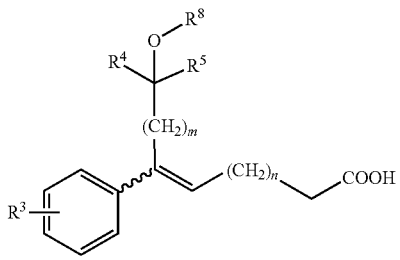

wherein, $R^3$, $R^4$, $R^5$, $R^8$, m and n are as defined above.

A compound represented by formula K:

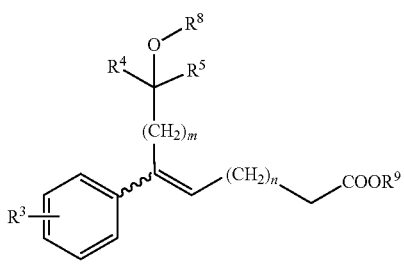

wherein, $R^3$, $R^4$, $R^5$, $R^8$, m and n are as defined above, and $R^9$ is methyl or ethyl A compound represented by formula J:

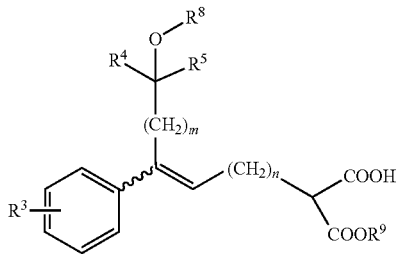

wherein, $R^3$, $R^4$, $R^5$, $R^8$, $R^9$, m and n are as defined above.

A compound represented by formula H:

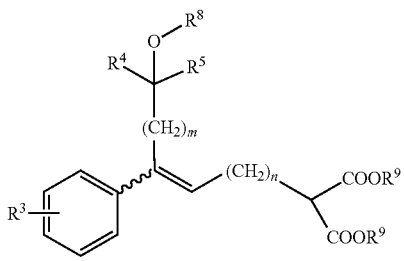

wherein, $R^3$, $R^4$, $R^5$, $R^8$, $R^9$, m and n are as defined above.

A compound represented by formula G:

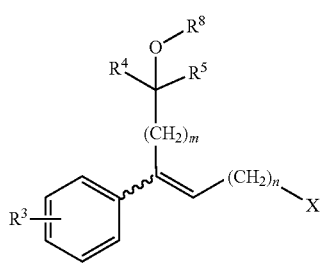

wherein, $R^3$, $R^4$, $R^5$, $R^8$, m and n are as defined above; X is halogen, i.e., fluorine, chlorine, bromine or iodine.

A compound represented by formula F:

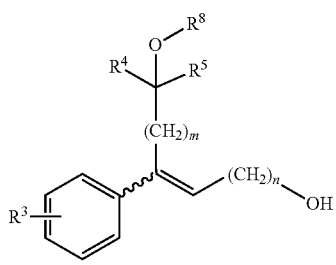

wherein, $R^3$, $R^4$, $R^5$, $R^8$, m and n are as defined above.

A compound represented by formula D:

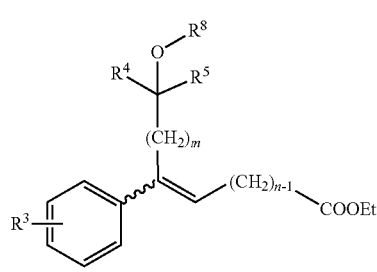

wherein, $R^3$, $R^4$, $R^5$, $R^8$, m and n are as defined above.

In addition, in the above mentioned intermediate compounds with carbon-carbon double bond, the carbon-carbon double bond is Z configuration or E configuration.

In yet another aspect, the present invention relates to a pharmaceutical composition comprising an effective amount of the compound represented by formula (I) and the pharmaceutically acceptable salt thereof.

The pharmaceutical composition of the present invention further comprises pharmaceutically acceptable carriers compatible with the compound of formula (I). The compound of formula (I) may be administered in general dosage forms, preferably oral dosage forms, such as, capsules, tablets, powders, flat capsules, suspensions or solutions. The dosage form and the pharmaceutical composition may be prepared by using traditional pharmaceutically acceptable excipients and additives and adopting traditional techniques. The pharmaceutically acceptable excipients and additives include non-toxic compatible fillers, binders, disintegrating agents, buffers, preservatives, antioxidants, lubricants, flavoring agents, thickening agents, colorants, emulsifiers and the like.

In another aspect, the present invention relates to use of the compound of formula (I) in preparation of a medicament for the reduction of serum cholesterol levels.

The present invention further relates to a method of reduction of serum cholesterol, said method comprises administration of an effective amount of compound of formula (I), that is, application of the compound of the present invention as a medicament to reduce serum cholesterol levels.

The compound of the present invention can decrease total cholesterol (TC) and low density lipoprotein cholesterol (LDL-C) levels in plasma, and can be used as a medicament for reduction of blood cholesterol. Therefore, the compound of the present invention can be used for treatment or prevention of diseases of atherosclerosis, vascular dysfunction, heart failure, coronary artery disease, cardiovascular disease, myocardial infarction, angina and hyperlipidaemia, hypercholesterolaemia and the like.

As used herein, some of the terms are as defined as follows.

"Halogen" refers to fluorine, chlorine, bromine and iodine.

"Alkyl" when used as a substituent or part of a substituent, refers to a linear or branched aliphatic hydrocarbon substituent. Most preferable one is $C_1$-$C_6$ alkyl, unless otherwise indicated. Examples of linear or branched $C_1$-$C_6$ alkyl include but not limited to methyl, ethyl, n-propyl, 2-propyl, n-butyl, isobutyl, tert-butyl, hexyl and the like.

"Alkenyl" when used as a substituent or part of a substituent, refers to an aliphatic hydrocarbon substituent with at least one carbon carbon double bond, and may be linear or branched. Most preferable one is $C_2$-$C_6$ alkenyl. The said substituent may contain multiple double bonds in its backbone which may independently be E configuration or Z configuration. Examples of said alkenyl include but not limited to vinyl, propenyl, allyl and the like.

"Cycloalkyl" refers to a saturated or partially saturated single, condensed or spiro carbon ring. Preferably, it is a ring with 3-6 carbon atoms. Examples include but not limited to cyclopropyl, cyclobutyl, cyclopentyl, cyclohexyl and the like.

"Alkoxy" refers to a substituent of (alkyl-O—), in which the alkyl is as defined herein. Preferably, it is $C_1$-$C_6$ alkoxy. Examples include but not limited to methoxy, ethoxy, n-propoxy, isopropoxy, n-butoxy, isobutoxy, tert-butoxy and the like.

The term "aryl", when used alone or in combination, refers to aromatic carbon-ring system with one or two rings, in which said rings may be fused connected. The term "aryl" includes aromatic groups such as phenyl, naphthyl and tetrahydronaphthyl. Preferred aryl is $C_6$-$C_{10}$ aryl, more preferred aryl is phenyl. Said "aryl" may have one or more substituents, such as $C_1$-$C_6$ alkyl, hydroxyl, halogen, alkylhalide, nitro, cyano, $C_1$-$C_6$ alkoxy, $C_1$-$C_6$ alkyl amino and the like.

The present invention includes the compound of formula (I) and various possible isomers thereof, which include non-mirror-image isomers, mirror-image isomers and geometric isomers such as the "Z" or "E" configurational isomers.

In addition, the term "pharmaceutically acceptable salt" refers to a salt of the compound that has original biological activities and is suitable for the medical use. The pharmaceutically acceptable salt of the compound of formula (I) is a salt formed with alkali metal. The alkali metal that can form a pharmaceutically acceptable salt with the compound of formula (I) includes lithium, sodium, potassium, magnesium, calcium, aluminum, zinc and the like.

The compound of formula (I) is preferably administered orally.

We have found that the compound of the present invention can reduce serum cholesterol levels.

Preparation of Azetidinone Compounds

Another aspect of the present invention further relates to preparation of the compound of formula (I), which comprises deprotection of a compound represented by formula V under basic conditions,

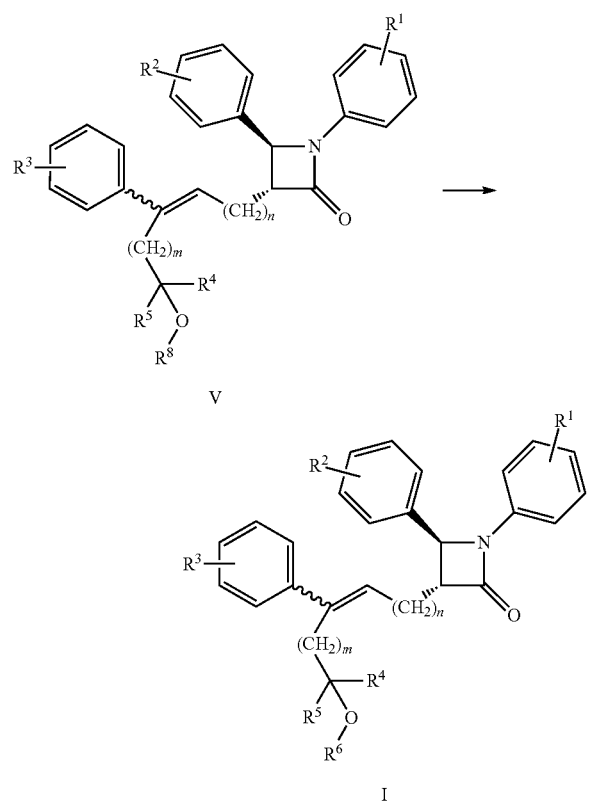

wherein $R^1$, $R^2$, $R^3$, $R^4$, $R^5$, $R^6$, m and n are as defined above, $R^8$ is a hydroxyl-protecting group, such as acetyl, tert-butyldimethylsilyl (TBDMS), trimethylsilyl (TMS), tert-butyldiphenylsilyl (TBDPS) or the like; when $R^2$ is hydroxyl, it is optionally protected, and after hydrolysis of the compound of formula V, the protecting group on $R^2$ is removed, alternatively, if necessary, the hydroxyl is further converted to other substituent as defined above for $R^2$.

The compound of formula V may be prepared by following method, the method comprises the treatment of a compound represented by formula IV with N,O-bis(trimethylsilyl)acetamide and subsequent cyclization of the resultant silylated product:

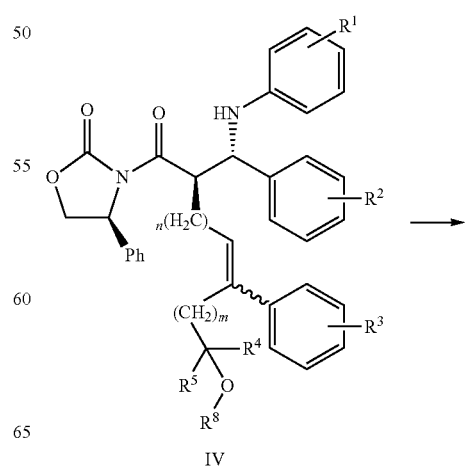

-continued

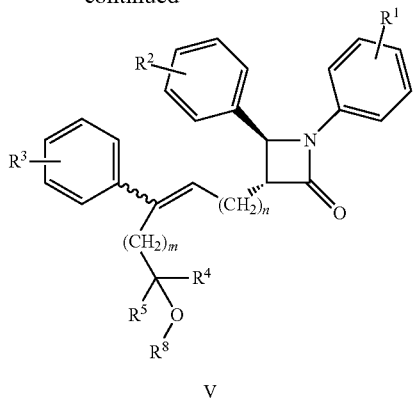

V wherein $R^1$, $R^2$, $R^3$, $R^4$, $R^5$, $R^8$, m and n are as defined above.

The compound of formula IV used above may be prepared by following method, in which a compound represented by formula III is dissolved in a suitable anhydrous solvent (such as anhydrous methylene chloride), then condensed with an imine represented by formula II under the protection of dry inert gas (such as nitrogen) with the presence of Lewis acid $TiCl_4$ as a catalyst;

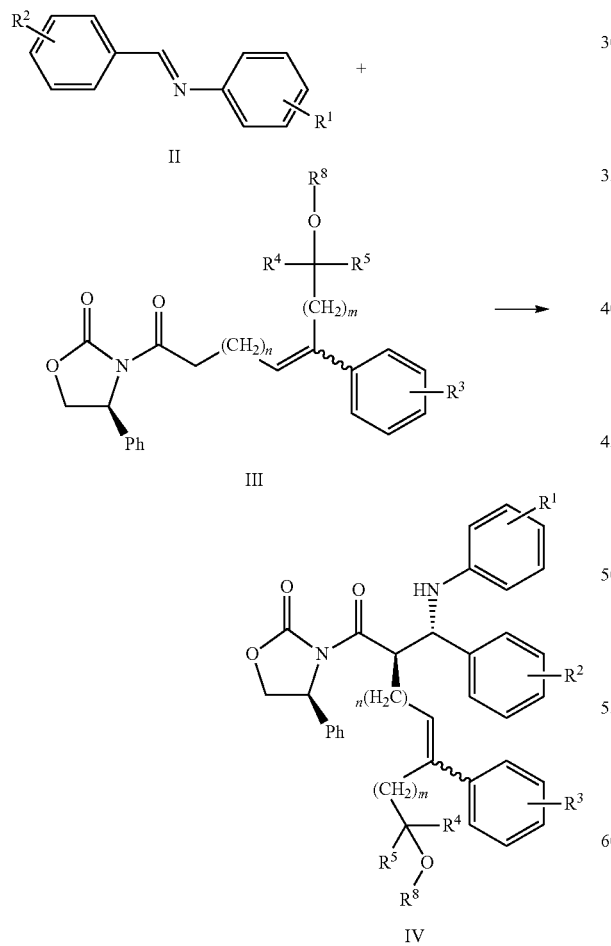

the compound of formula III used above may be prepared by following method, in which in a anhydrous inert solvent (such as $CH_2Cl_2$ or THF), an acid represented by formula L and isobutyl chloroformate form mixed anhydride, and then condensed with (S)-4-phenyl-2-oxazolidinone under the presence of a suitable catalyst (such as sodium bis(trimethylsily)amide or 4-dimethylaminopyridine (DMAP), preferably sodium bis(trimethylsilyl)amide at temperature of −60° C. to −25° C.;

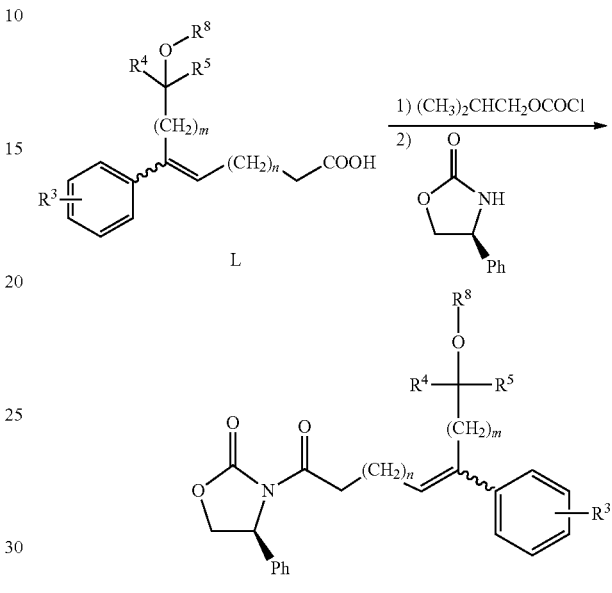

the compound of formula L used above may be prepared by following method, in which a compound represented by formula K is hydrolysed under basic conditions, and then is acidified to obtain the compound of formula L;

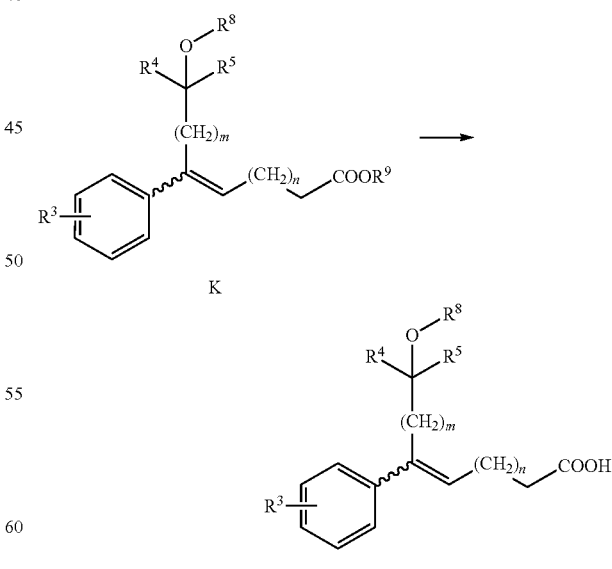

wherein, $R^9$ is methyl or ethyl.

The compound of formula K used above may be prepared by following method, in which a compound represented by formula J is decarboxylated by heating to obtain a single ester compound, i.e., the compound of formula K;

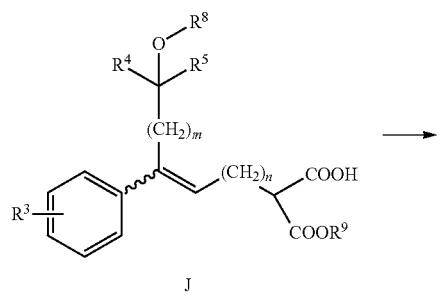

J

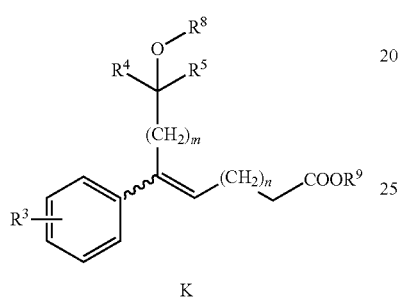

K the compound of formula J used above may be prepared by following method, in which a compound represented by formula H is hydrolyzed on a single ester under a controlled suitable reaction conditions to obtain the compound of formula J;

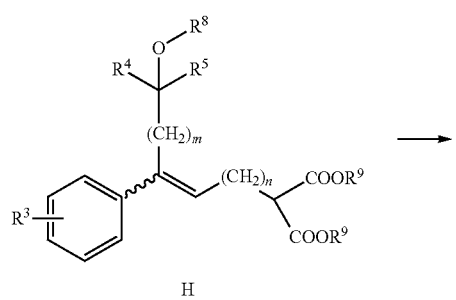

H

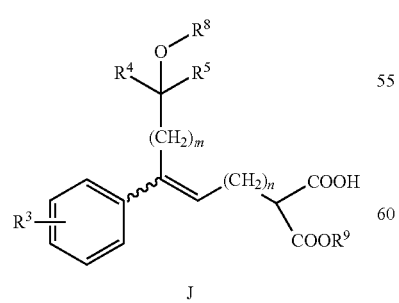

J the compound of formula H used above may be prepared by following method, in which a compound represented by formula G is reacted with diester malonate to obtain the diester compound of formula H;

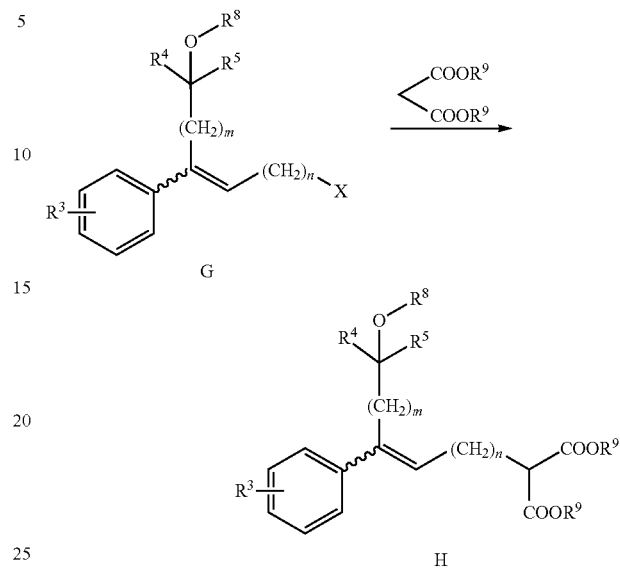

wherein, X is halogen, that is fluorine, chlorine, bromine or iodine.

The compound of formula G used above may be prepared by following method, in which the hydroxyl of a compound represented by formula F is halogenated via treatment of halogenated agent to obtain the compound of formula G;

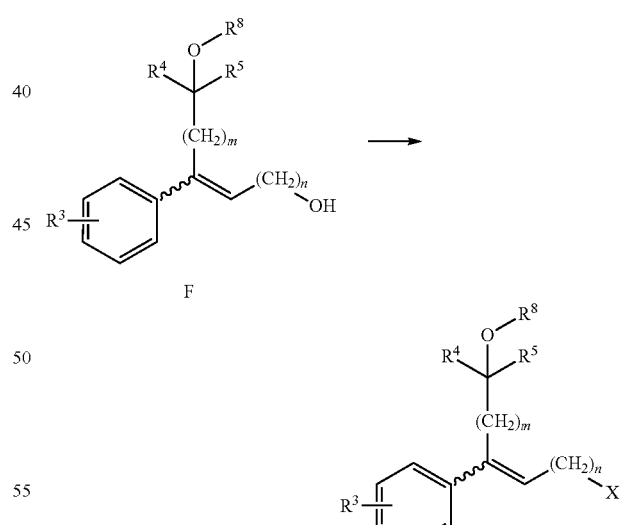

the compound of formula F used above may be prepared by the following method, in which the ester group of a compound represented by formula D is reduced by a suitable reducing agent (such as diisobutylaluminum hydride (DIBAH)) to obtain the compound of formula F;

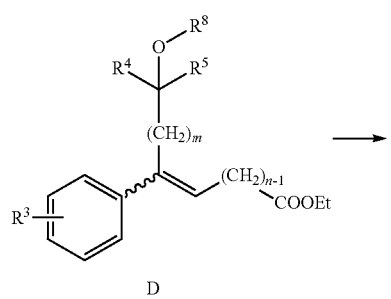

D

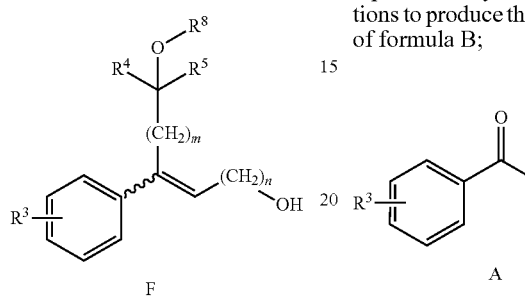

F the compound of formula D used above may be prepared by following method, in which a compound represented by formula C is subjected to Wittig-Horner reaction to produce the compound of formula D, which is further separated to obtain Z configuration and E configuration;

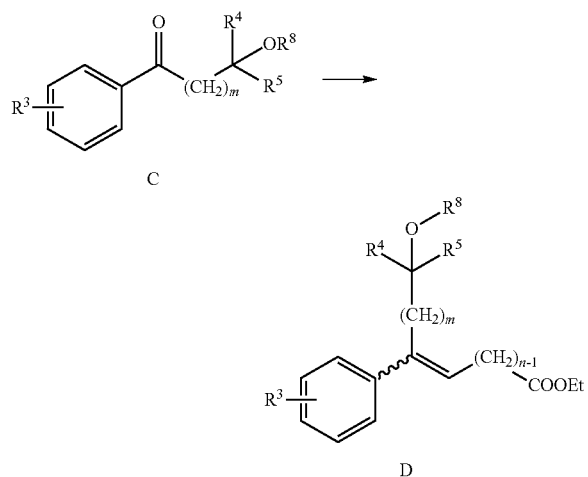

the compound of formula C used above may be prepared by following method, in which in a suitable solvent, the hydroxyl of a compound represented by formula B is protected with the presence of suitable catalysts (such as 4-dimethylaminopyridine (DMAP)) to produce the compound of formula C;

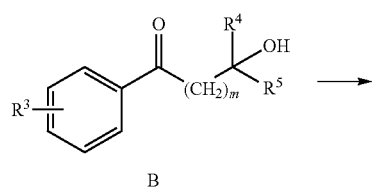

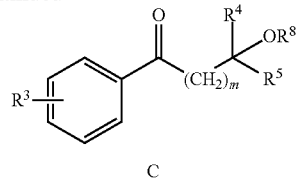

C the compound of formula B used above may be prepared by following method, in which the ester group in a compound represented by formula A is hydrolyzed under basic conditions to produce the corresponding alcohol, i.e. the compound of formula B;

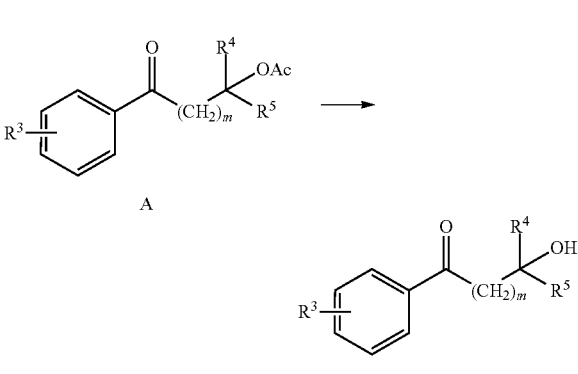

the compound of formula A used above may be prepared by following method, in which a halide is reacted with sodium acetate to produce the compound of formula A;

The present invention are further illustrated by the following examples. The examples provide the preparation of typical compounds represented by formula (I) and relevant data of structural identifications thereof. It should be noted that the following examples are illustrative only, and are not to be construed as limiting the present invention in any way.

In the following examples, unless otherwise indicated, all temperatures are Celsius; and unless otherwise specified, all of starting raw materials and reagents were commercially available. The commercially available raw materials and reagents were used directly without further purification, unless otherwise specified.

Glasswares were dried with oven and/or by heating. Reactions were traced on silica glass-60 F254 plate (0.25 mm) (TLC), which was an analytical thin layer chromatography and was developed with an appropriate ratio (V/V) of solvents. The end a reaction was determined when starting materials on TLC were exhausted.

$^1$H NMR spectra were determined by using Bruker instrument (400 MHz). The chemical shift was represented by ppm. Tetramethylsilane was used as the internal reference (0.00 ppm). $^1$H NMR was represented as the following: s=singlet, d=doublet, t=triplet, m=multiplet, br=broad, dd=doublet of doublet, dt=doublet of triplet. When coupling constant was provided, its unit was Hz.

Mass spectra were determined by LC/MS instrument with ionization of ESI or APCI.

None of melting points was corrected.

The following examples are only illustrative of the synthesis process of specific compounds of the present invention. However, there is no limit in the synthesis process. Compounds not listed hereinafter can also be prepared with the same synthesis route and the same synthesis process by selecting appropriate starting raw materials, and making necessary adjustments on some reaction conditions, which can be known from common knowledge.

Synthesis

As for the compound of formula (I), when $R^1=R^3=F$, $R^2=OH$, $R^4=R^5=R^6=H$, $R^8=TBDMS$, $R^9=Me$, $X=Cl$, $m=0$, $n=1$, the corresponding compound may be synthesized by using the process shown in the following synthetic route.

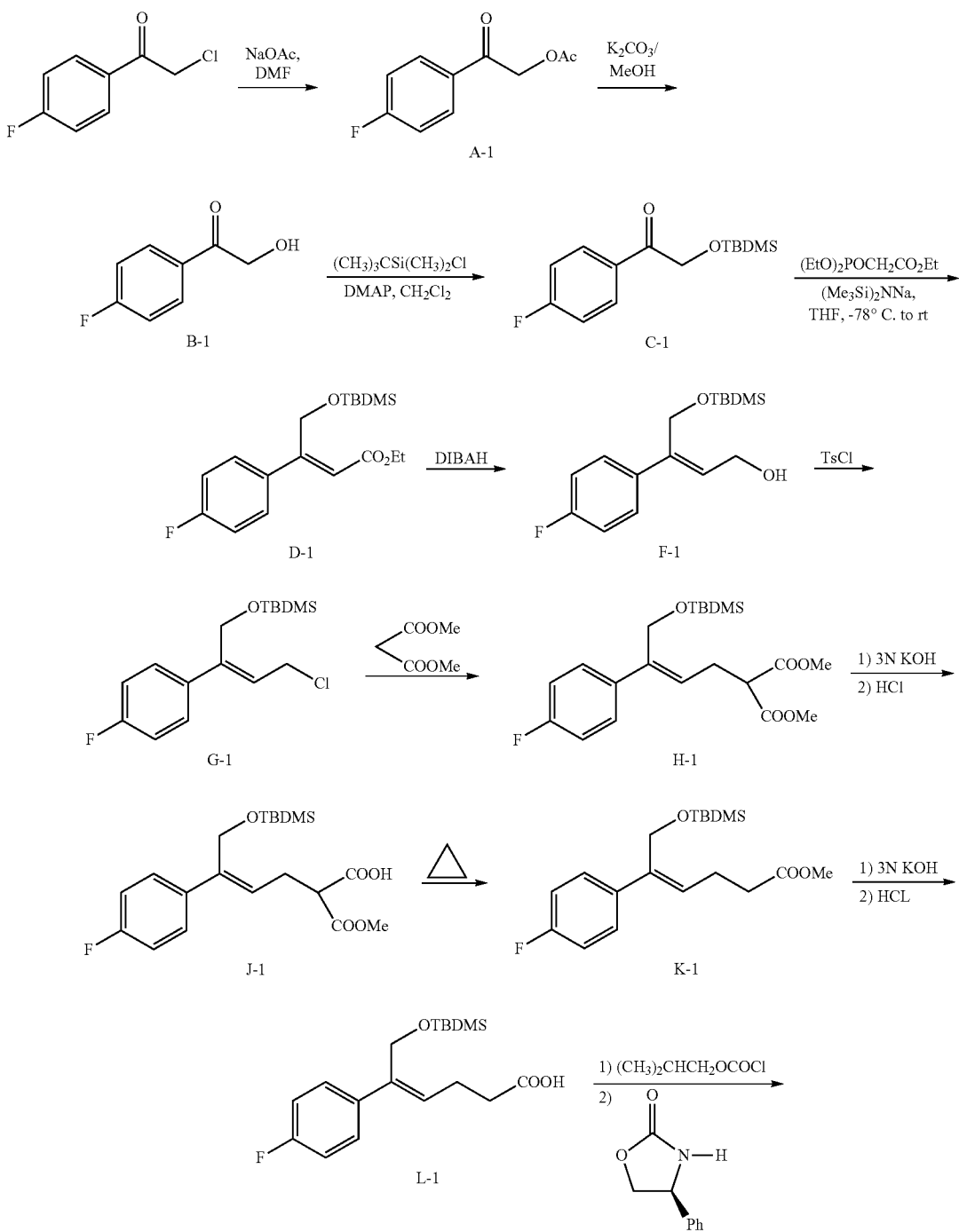

-continued
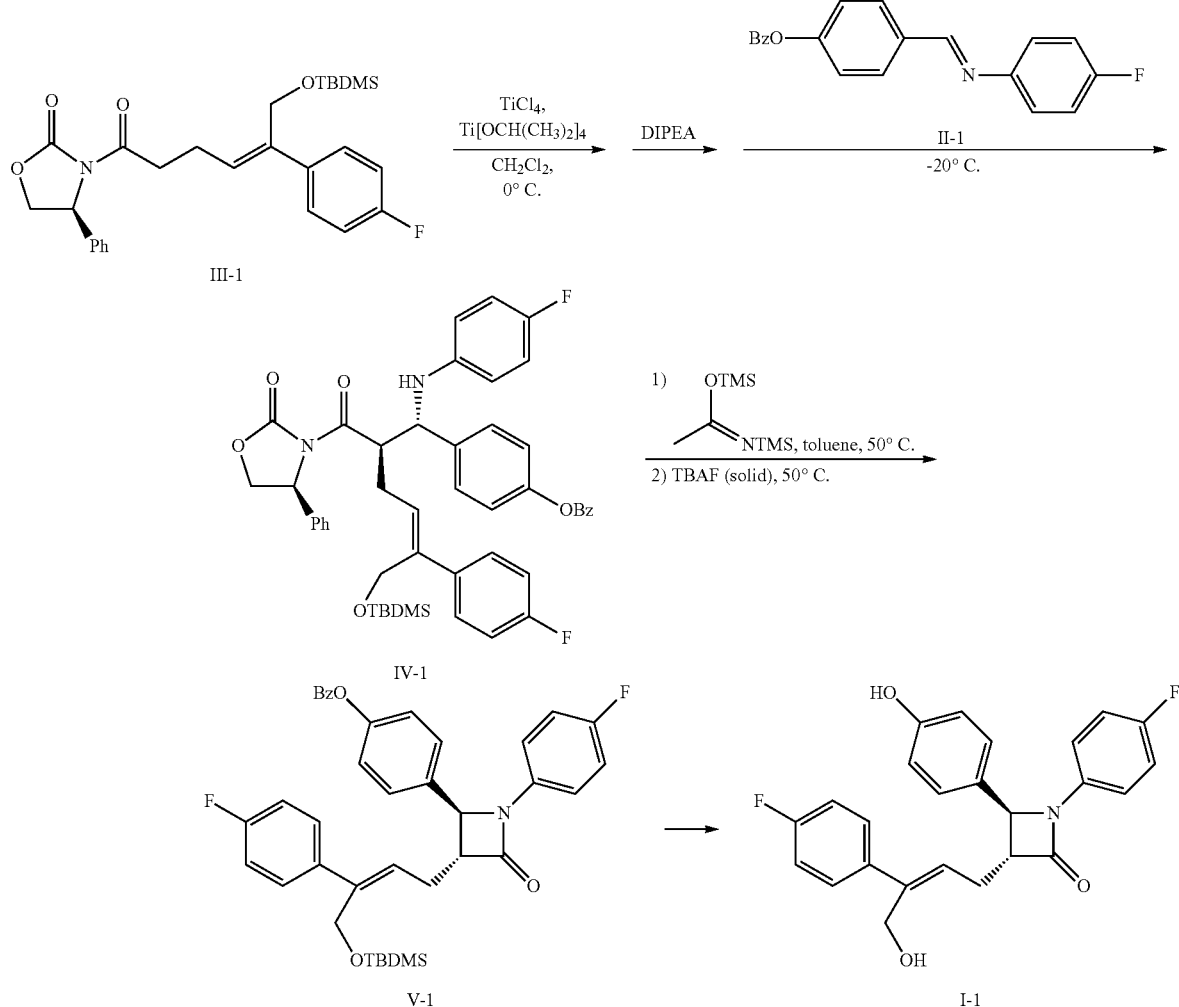
The compound of II-1 may be synthesized through the following process:
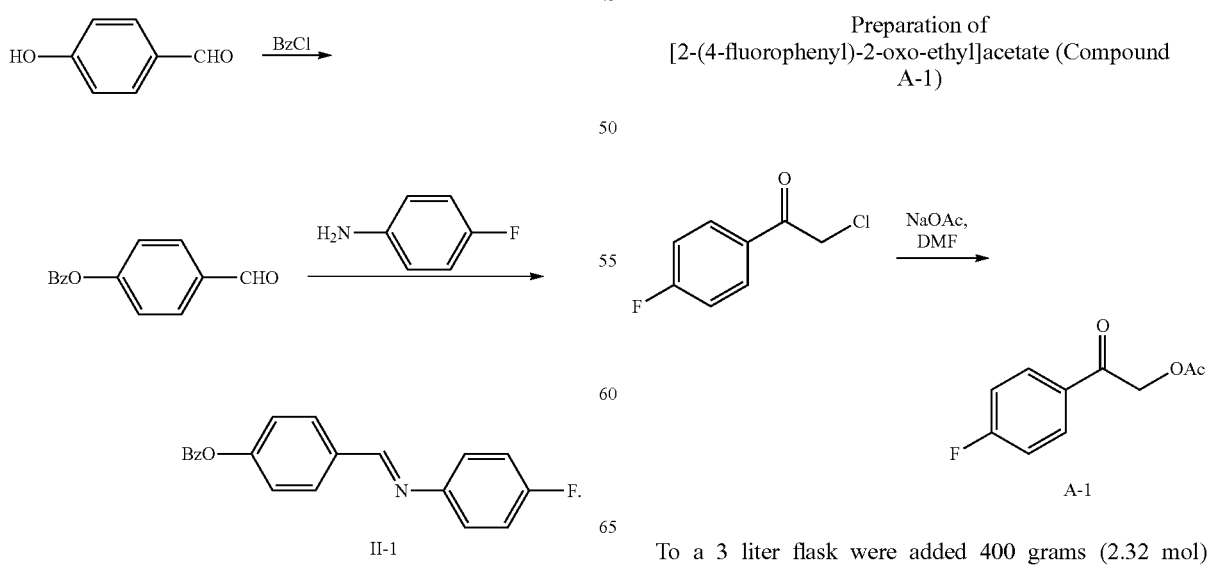
DETAILED EMBODIMENTS
Example 1
Preparation of [2-(4-fluorophenyl)-2-oxo-ethyl]acetate (Compound A-1)
To a 3 liter flask were added 400 grams (2.32 mol) 2-chloro-1-(4-fluorophenyl)ethanone, 1 liter of N,N-dimethylformamide and 265 grams (3.23 mol) anhydrous sodium acetate. The mixture was stirred and heated to 90° C., and the reaction lasted 10 hours. After the reaction was completed, the heating was stopped. The reaction solution was cooled down to room temperature, and extracted with ethyl acetate (600 ml×6). The organic phases were combined, washed three times with brine, dried over anhydrous sodium sulfate and concentrated until dry. The residue was crystallized from the mixed toluene/petroleum ether solution and dried to obtain 357 grams (1.82 mol) compound A-1 with yield of 78.5%. $^1$H NMR (400 MHz, CDCl$_3$): δ 2.23 (s, 3H, CH$_3$), 5.30 (s, 2H, —CH$_2$—), 7.14-7.19 (m, 2H, Cpr-H), 7.93-7.97 (m, 2H, Cpr-H); MS (m/z): 197 [M+H].

Example 2

Preparation of 1-(4-fluorophenyl)-2-hydroxy-ethanone (Compound B-1)

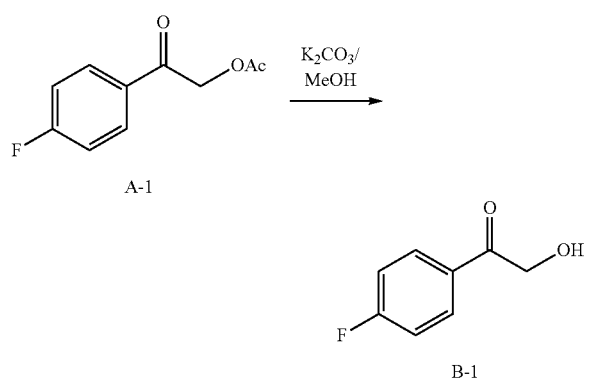

To a 2 liter flask were added 321.3 grams (1.64 mol) compound A-1, 1 liter of methanol, 18 grams (0.13 mol) potassium carbonate. The mixture was stirred at room temperature and the reaction lasted 2 hours. The mixture was extracted 5 times with ethyl acetate (800 ml×5). The organic phases were combined, dried over anhydrous sodium sulfate, and concentrated until dry to obtain 211.0 grams (1.37 mol) compound B-1 with yield of 83.5%. $^1$H NMR (400 MHz, CDCl$_3$): δ 3.46 (t, 1H, J=4.4 Hz, —OH), 4.85 (d, 2H, J=4.1 Hz, —CH$_2$—), 7.17-7.21 (m, 2H, Cpr-H), 7.95-7.98 (m, 2H, Cpr-H).

Example 3

Preparation of 2-tert-butyldimethylsilyloxy-1-(4-fluorophenyl)ethanone (Compound C-1)

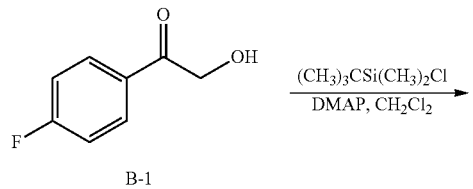

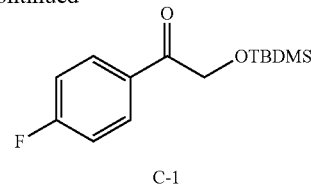

To a 5 liter flask were added 187.8 grams (1.22 mol) compound B-1, 1.2 liters of acetonitrile, 1.8 liters of dichloromethane, 17.6 grams (0.14 mol) 4-dimethylaminopyridine (DMAP), 200 ml (1.44 mol) of triethylamine and 258.4 grams (1.72 mol) tert-butyldimethylsilane chloride (TBDMSCl). The mixture was stirred at room temperature and the reaction lasted 10 hours. Then, 136 ml (1 mol/L) of hydrochloric acid was added dropwise into the reaction solution. After the addition, the reaction solution was further stirred for 20 minutes, and then extracted 3 times with dichloromethane (400 ml×3). The organic phases were combined and washed 5 times with brine, dried over anhydrous sodium sulfate and concentrated until dry. The residue was purified by column chromatography (petroleum ether/dichloromethane=1.5/1) to obtain 219.5 grams (0.82 mol) compound C-1 with yield of 67.2%. $^1$H NMR (400 MHz, CDCl$_3$): δ 0.16 (s, 6H, 2×-CH$_3$), 0.93 (s, 9H, 3×-CH$_3$), 4.86 (s, 2H, —CH$_2$—), 7.11-7.15 (m, 2H, Cpr-H), 7.96-8.00 (m, 2H, Cpr-H); MS (m/z): 269 [M+H].

Example 4

Preparation of ethyl 4-tert-butyldimethylsilyloxy-3-(4-fluorophenyl) but-2-enoate (Compound D-1)

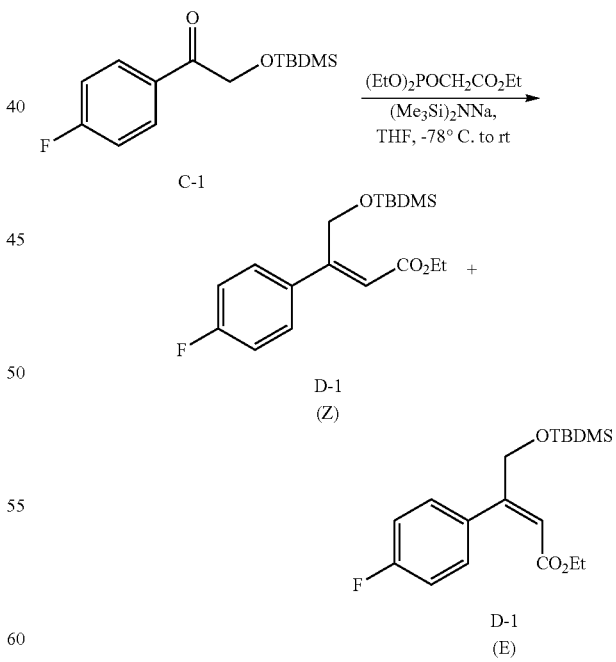

To a 5 liter flask were added 27.0 grams (1.19 mol) triethyl phosphonoacetate and 1.3 liters of tetrahydrofuran. The mixture was stirred, and 0.82 liters (2 mol/L) sodium bis(trimethylsilyl)amide was added dropwise at about −30° C. After the addition, the mixture was warmed up to room temperature and the reaction lasted 1 hour. Then, 192.1 grams (0.72 mol) compound C-1 (dissolved in 450 ml of tetrahydrofuran) was added dropwise at a temperature of about −60° C. After the addition, the temperature was raised to room temperature and the reaction lasted 1 hour. The resultant was extracted 3 times with ethyl acetate (250 ml×3), dried over anhydrous sodium sulfate, and concentrated until dry. The product was purified by column chromatography (petroleum ether) to obtain 125 grams (0.37 mol, yield 51.4%) compound D-1 (Z configuration) and 67.6 grams (0.20 mol, yield 27.8%) compound D-1 (E configuration). Compound D-1 (Z configuration): $^1$H NMR (400 MHz, CDCl$_3$): δ −0.11 (s, 6H, 2×-CH$_3$), 0.65 (s, 9H, 3×-CH$_3$), 1.21 (t, 3H, J=7.2 Hz, —CH$_3$), 4.09 (d, 1H, J=7.2 Hz, —CH$_2$—), 4.12 (d, 1H, J=7.1 Hz, —CH$_2$—), 5.06 (d, 2H, J=1.0 Hz, —CH$_2$—), 5.89 (s, 1H, —CH—), 6.90-6.95 (m, 2H, Cpr-H), 7.35-7.38 (m, 2H, Cpr-H); MS (m/z): 339 [M+H]. Compound D-1 (E configuration): $^1$H NMR (400 MHz, CDCl$_3$): δ 0.10 (s, 6H, 2×-CH$_3$), 0.94 (s, 9H, 3×-CH$_3$), 1.10 (t, 3H, J=7.2 Hz, —CH$_3$), 4.00 (d, 1H, J=7.2 Hz, —CH$_2$—), 4.03 (d, 1H, J=7.1 Hz, —CH$_2$—), 4.30 (s, 2H, —CH$_2$—), 6.20 (s, 1H, —CH—), 7.02-7.06 (m, 2H, Cpr-H), 7.13-7.16 (m, 2H, Cpr-H); MS (m/z): 339 [M+H].

Example 5

Preparation of (Z)-4-tert-butyldimethylsilyloxy-3-(4-fluorophenyl)but-2-en-1-ol (Compound F-1, Z Configuration)

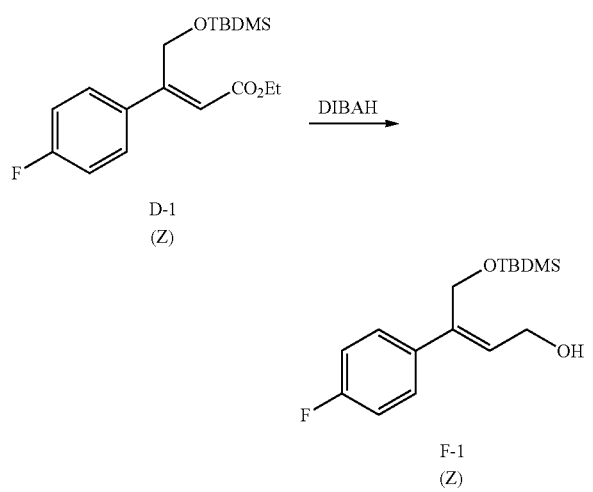

To a 5 liter flask were added 120 grams (0.36 mol) compound D-1 (Z configuration) and 1.0 liter of dichloromethane. Then, 0.8 liter (1.125 mol/L) of diisobutylaluminium hydride (DIBAH) n-hexane solution was added dropwise at about −60° C. The temperature was warm to room temperature and the reaction lasted 30 minutes. 500 ml of dichloromethane was added to the reaction solution. The resultant was washed sequentially with saturated ammonium chloride solution, then brine for 3 times, dried over anhydrous sodium sulfate and concentrated till dry to obtain 103.6 grams (0.35 mol) compound F-1 (Z configuration) with yield of 97.2%. $^1$H NMR (400 MHz, CDCl$_3$): δ 0.07 (s, 6H, 2×-CH$_3$), 0.86 (s, 9H, 3×-CH$_3$), 2.25 (t, 1H, J=5.8 Hz, —OH), 4.36 (t, 2H, J=6.3 Hz, —CH$_2$—), 4.54 (s, 2H, —CH$_2$—), 5.99 (t, 1H, J=6.8 Hz, —CH—), 6.98-7.02 (m, 2H, Cpr-H), 7.32-7.36 (m, 2H, Cpr-H).

Example 6

Preparation of (E)-4-tert-butyldimethylsilyloxy-3-(4-fluorophenyl)but-2-en-1-ol (Compound F-1, E Configuration)

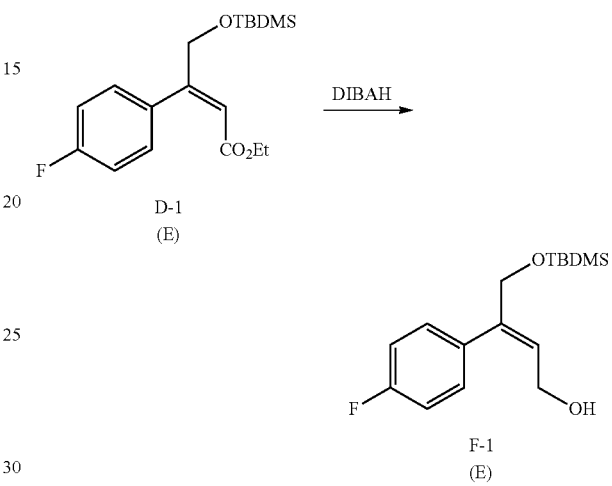

The said compound is prepared from ethyl (E)-4-tert-butyldimethylsilyloxy-3-(4-fluorophenyl)-but-2-enoate (compound D-1, E configuration) according to the similar process as Example 5. $^1$H NMR (400 MHz, CDCl$_3$): δ 0.09 (s, 6H, 2×-CH$_3$), 0.94 (s, 9H, 3×-CH$_3$), 4.12-4.14 (m, 2H, —CH$_2$—), 4.34 (s, 2H, —CH$_2$—), 6.01 (t, 1H, J=6.8 Hz, —CH—), 7.05-7.09 (m, 2H, Cpr-H), 7.16-7.19 (m, 2H, Cpr-H).

Example 7

Preparation of tert-butyl-[(Z)-4-chloro-2-(4-fluorophenyl)but-2-enoxy]-dimethyl-silane (Compound G-1, Z Configuration)

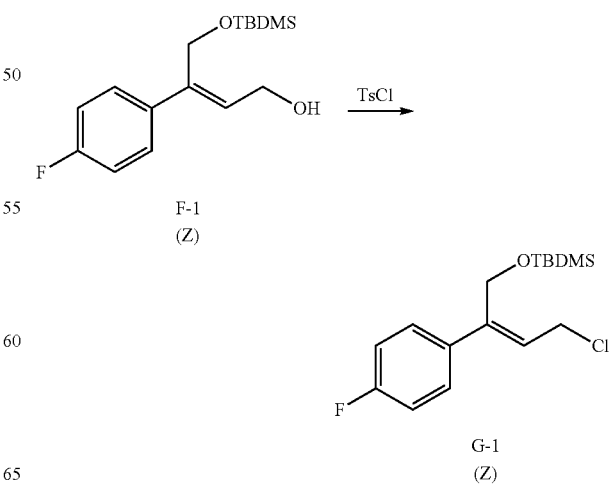

To a 5 liter flask were added 100.6 grams (0.34 mol) of compound F-1 (Z configuration), 1.6 liters of dichloromethane, 10.5 grams (0.085 mol) 4-dimethylamiopryidine and 182 ml of diisopropylethylamine. The mixture was stirred under the protection of nitrogen, in which 74.3 grams (0.39 mol) 4-toluenesulfonyl chloride (TsCl) (dissolved in 800 ml of dichloromethane) was added dropwise at about −20° C. The solution was warmed up to room temperature and the reaction lasted 12 hours. Then the reaction solution was acidified to pH=4 with 2 mol/L of hydrochloric acid. The reaction solution was stirred for 30 minutes, then layered. The aqueous phase was extracted 2 times with dichloromethane (100 ml×2). The obtained organic phases were combined, washed 3 times with brine, dried over anhydrous sodium sulfate and concentrated till dry to obtain 77.5 grams (0.25 mol) compound G-1 (Z configuration) with yield of 73.5%. $^1$H NMR (400 MHz, CDCl$_3$): δ 0.06 (s, 6H, 2×-CH$_3$), 0.88 (s, 9H, 3×-CH$_3$), 4.34 (d, 2H, J=8.0 Hz, —CH$_2$—), 4.57 (s, 2H, —CH$_2$—), 5.91 (t, 1H, J=8.0 Hz, —CH—), 6.99-7.03 (m, 2H, Cpr-H), 7.35-7.39 (m, 2H, Cpr-H).

Example 8

Preparation of tert-butyl-[(E)-4-chloro-2-(4-fluorophenyl)but-2-enoxy]-dimethyl-silane (Compound G-1, E Configuration)

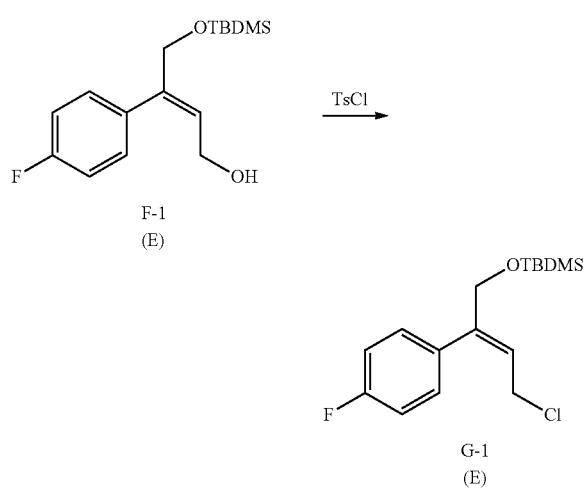

The title compound was prepared from (E)-4-tert-butyldimethylsilyloxy-3-(4-fluorophenyl)but-2-en-1-ol (compound F-1 E configuration) according to the similar process as Example 7. $^1$H NMR (400 MHz, CDCl$_3$): δ 0.07 (s, 6H, 2×-CH$_3$), 0.91 (s, 9H, 3×-CH$_3$), 3.97-3.99 (m, 2H, —CH$_2$—), 4.30 (s, 2H, —CH$_2$—), 5.99 (t, 1H, J=8.0 Hz, —CH—), 7.04-7.09 (m, 2H, Cpr-H), 7.17-7.21 (m, 2H, Cpr-H).

Example 9

Preparation of dimethyl 2-[(Z)-4-tert-butyldimethyl-silyloxy-3-(4-fluorophenyl)but-2-enyl]propanedioate (Compound H-1, Z Configuration)

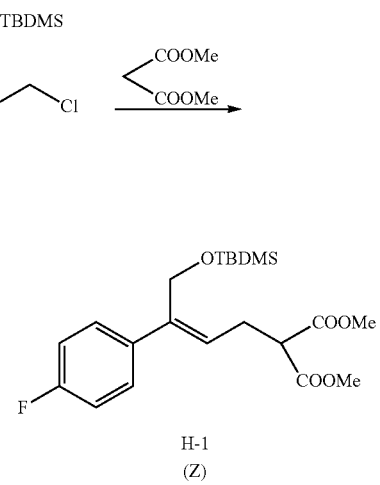

To a 3 liter flask were added 57.2 grams (0.43 mol) dimethyl malonate and 1 liter of N,N-dimethylformamide. The mixture was stirred under the protection of nitrogen, in which 73.0 grams (0.55 mol) cesium carbonate was added at room temperature. After reacting 2 hours at room temperature, 75.5 grams (0.24 mol) of compound G-1 (Z configuration) (dissolved in 300 ml of N,N-dimethylformamide) was added therein dropwise. After reacting for 1 hour, 400 ml of ethyl acetate and 100 ml of water were added to the reaction solution. The solution was layered. The aqueous layer was extracted 3 times with ethyl acetate (100 ml×3). The organic phases were combined, washed 3 times with brine, dried over anhydrous sodium sulfate and concentrated till dry to obtain 96.5 grams (0.235 mol) compound H-1 (Z configuration) with yield of 98%. $^1$H NMR (400 MHz, DMSO-d$_6$): δ 0.01 (s, 6H, 2×-CH$_3$), 0.81 (s, 9H, 3×-CH$_3$), 2.84 (t, 2H, J=7.6 Hz, —CH$_2$—), 3.50 (t, 1H, J=7.6 Hz, —CH—), 3.73 (s, 6H, 2×-CH$_3$), 4.50 (s, 2H, —CH$_2$—), 5.62 (t, 1H, J=7.6 Hz, —CH—), 6.93-6.97 (m, 2H, Cpr-H), 7.27-7.31 (m, 2H, Cpr-H); MS (m/z): 411 [M+H].

Example 10

Preparation of dimethyl 2-[(E)-4-tert-butyldimethyl-silyloxy-3-(4-fluorophenyl)but-2-enyl]propanedioate (Compound H-1, E Configuration)

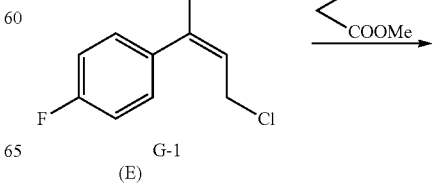

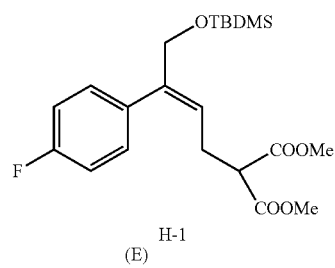

The title compound was prepared from tert-butyl-[(E)-4-chloro-2-(4-fluorophenyl)but-2-enoxy]-dimethyl-silane (compound G-1 E configuration) according to the similar process as Example 9. $^1$H NMR (400 MHz, CDCl$_3$): δ 0.03 (s, 6H, 2×-CH$_3$), 0.90 (s, 9H, 3×-CH$_3$), 2.54 (t, 2H, J=7.6 Hz, —CH$_2$—), 3.39 (t, 1H, J=7.6 Hz, —CH—), 3.71 (s, 6H, 2×-CH$_3$), 4.24 (s, 2H, —CH$_2$—), 5.67 (t, 1H, J=7.6 Hz, —CH—), 7.02-7.07 (m, 2H, Cpr-H), 7.10-7.14 (m, 2H, Cpr-H); MS (m/z): 411 [M+H].

Example 11

Preparation of (Z)-6-tert-butyldimethylsilyloxy-5-(4-fluorophenyl)-2-methoxycarbonyl-hex-4-enoic acid (Compound J-1, Z Configuration)

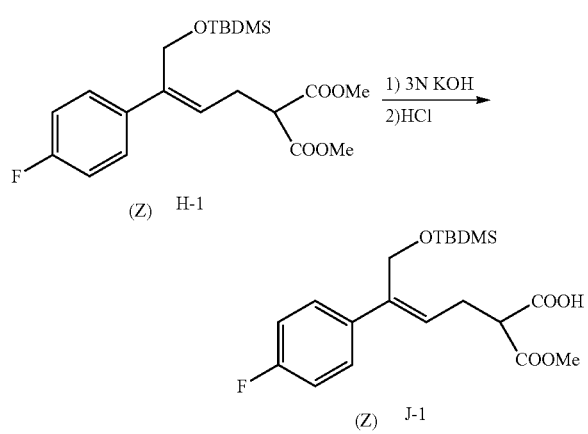

To a 2 liter flask were added 94.0 grams (with content being 75%, 0.23 mol) compound II-1 (Z configuration) and 0.62 liter of ethanol. Then, 85 ml of 3 mol/L potassium hydroxide aqueous solution was added dropwise at room temperature. After reacting for 1 hour, the reaction solution was acidified to pH=4 with 2 mol/L of hydrochloric acid. The mixture was stirred for 30 minutes, and extracted 3 times with ethyl acetate (150 ml×3). The organic phases were combined, washed 3 times with brine, dried over anhydrous sodium sulfate and concentrated till dry to obtain 76.1 grams (0.19 mol) of compound J-1 (Z configuration) with yield of 83.8%. $^1$H NMR (400 MHz, CDCl$_3$): δ 0.01 (s, 6H, 2×-CH$_3$), 0.80 (s, 9H, 3×-CH$_3$), 2.84-2.87 (m, 2H, —CH$_2$—), 3.53 (t, 1H, J=7.2 Hz, —CH—), 3.74 (s, 3H, —CH$_3$), 4.49 (s, 2H, —CH$_2$—), 5.62 (t, 1H, J=7.2 Hz, —CH—), 6.92-6.96 (m, 2H, Cpr-H), 7.23-7.30 (m, 2H, Cpr-H); MS (m/z): 397 [M+H].

Example 12

Preparation of (E)-6-tert-butyldimethylsilyloxy-5-(4-fluorophenyl)-2-methoxycarbonyl-hex-4-enoic acid (Compound J-1, E Configuration)

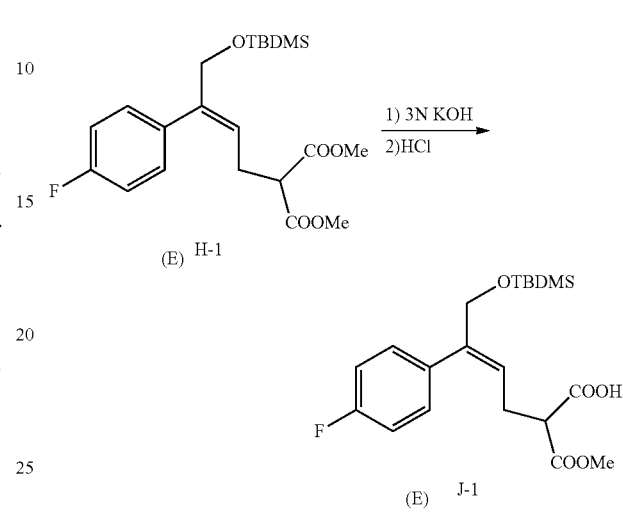

The title compound was prepared from dimethyl 2-[(E)-4-tert-butyldimethylsilyloxy-3-(4-fluorophenyl)but-2-enyl]propanedioate (compound II-1, E configuration) according to the similar process as Example 11. $^1$H NMR (400 MHz, CDCl$_3$): δ 0.02 (s, 6H, 2×-CH$_3$), 0.86 (s, 9H, 3×-CH$_3$), 2.56-2.60 (m, 2H, —CH$_2$—), 3.38 (t, 1H, J=7.2 Hz, —CH—), 3.70 (s, 3H, —CH$_3$), 4.20 (s, 2H, —CH$_2$—), 5.66 (t, 1H, J=7.2 Hz, —CH—), 6.99-7.03 (m, 2H, Cpr-H), 7.06-7.24 (m, 2H, Cpr-H); MS (m/z):419 [M+Na].

Example 13

Preparation of methyl (Z)-6-tert-butyldimethylsilyloxy-5-(4-fluorophenyl)hex-4-enoate (Compound K-1, Z Configuration)

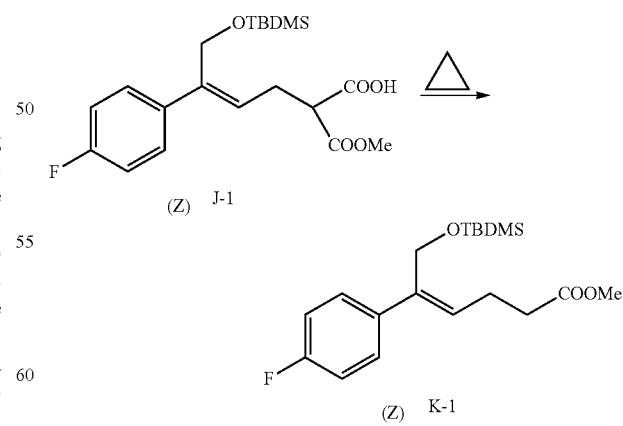

To a 2 liter flask were added 73.66 grams (0.186 mol) compound J-1 (Z configuration), 0.6 liter of toluene and 3.8 ml of triethylamine. The mixture was heated to reflux and the reaction lasted 5 hours. The resultant was extracted with ethyl acetate, washed with brine, dried over anhydrous sodium sulfate and concentrated till dry to obtain 57.02 grams (0.162 mol) of compound K-1 (Z configuration) with yield of 87.1%. $^1$H NMR (400 MHz, CDCl$_3$): δ 0.03 (s, 6H, 2×-CH$_3$), 0.84 (s, 9H, 3×-CH$_3$), 2.45-2.47 (m, 2H, —CH$_2$—), 2.56-2.61 (m, 2H, —CH$_2$—), 3.69 (s, 3H, —CH$_3$), 4.52 (s, 2H, —CH$_2$—), 5.70 (t, 1H, J=7.2 Hz, —CH—), 6.95-7.00 (m, 2H, Cpr-H), 7.33-7.36 (m, 2H, Cpr-H); MS (m/z): 353 [M+H].

Example 14

Preparation of methyl (E)-6-tert-butyldimethylsilyloxy-5-(4-fluorophenyl)hex-4-enoate (Compound K-1, E Configuration)

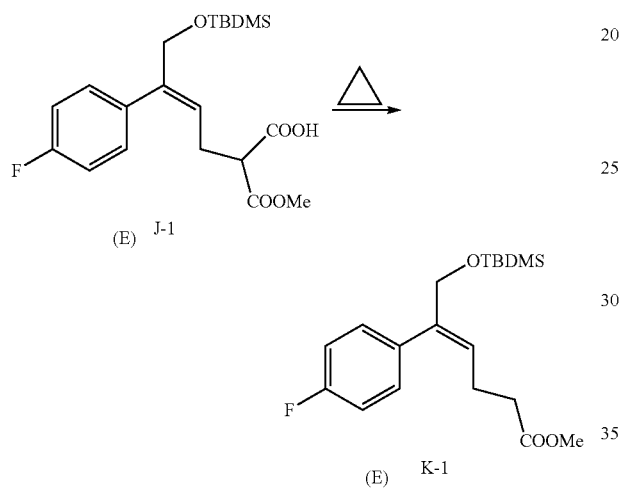

The title compound was prepared from 6-tert-butyldimethylsilyloxy-5-(4-fluorophenyl)-2-methoxycarbonyl-4(E)-hexenoic acid (compound J-1, E configuration) according to the similar process as Example 13. $^1$H NMR (400 MHz, CDCl$_3$): δ 0.02 (s, 6H, 2×-CH$_3$), 0.88 (s, 9H, 3×-CH$_3$), 2.27-2.33 (m, 4H, 2×-CH$_2$—), 3.64 (s, 3H, —CH$_3$), 4.24 (s, 2H, —CH$_2$—), 5.70 (t, 1H, J=7.2 Hz, —CH—), 7.02-7.05 (m, 2H, Cpr-H), 7.10-7.12 (m, 2H, Cpr-H); MS (m/z): 353 [M+H].

Example 15

Preparation of (Z)-6-tert-butyldimethylsilyloxy-5-(4-fluorophenyl)hex-4-enoic acid (Compound L-1, Z Configuration)

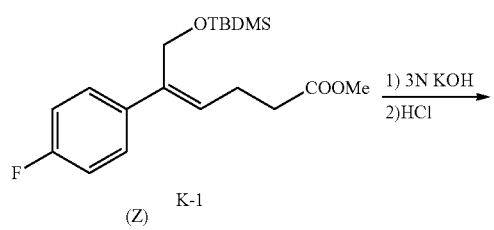

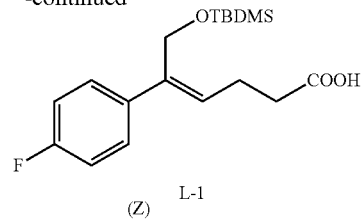

To a 1 liter flask were added 56.07 grams (0.159 mol) compound K-1 (Z configuration) and 180 ml of ethanol. Then, 54.28 ml (3 mol/L) of potassium hydroxide aqueous solution was added therein dropwise at room temperature. After reacting for 1 hour, the reaction solution was acidified to pH=4 with 2 mol/L of hydrochloric acid. The solution was continued stirring for 30 minutes. The residue was extracted 3 times with ethyl acetate (60 ml×3). The organic phases were combined, washed 3 times with brine, dried over anhydrous sodium sulfate and concentrated until dry to obtain 39.88 grams (0.118 mol) compound L-1 (Z configuration) with yield of 74.1%. $^1$H NMR (400 MHz, CDCl$_3$): δ 0.03 (s, 6H, 2×-CH$_3$), 0.84 (s, 9H, 3×-CH$_3$), 2.50-2.54 (m, 2H, —CH$_2$—), 2.57-2.61 (m, 2H, —CH$_2$—), 4.52 (s, 2H, —CH$_2$—), 5.74 (t, 1H, J=7.6 Hz, —CH—), 6.95-6.99 (m, 2H, Cpr-H), 7.32-7.36 (m, 2H, Cpr-H); MS (m/z): 361 [M+Na].

Example 16

Preparation of (E)-6-tert-butyldimethylsilyloxy-5-(4-fluorophenyl)hex-4-enoic acid (Compound L-1, E Configuration)

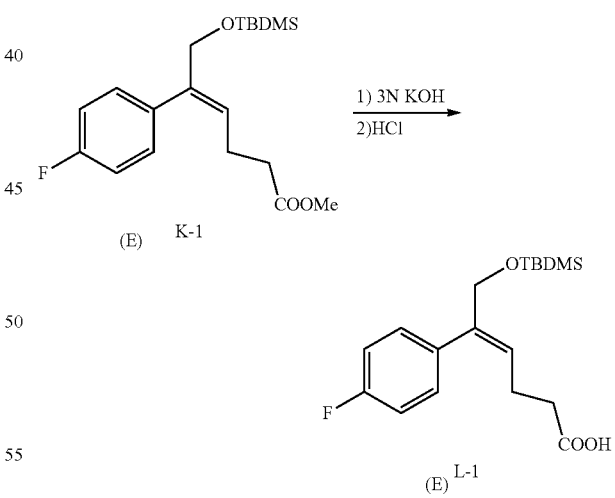

The title compound was prepared from methyl (E)-6-tert-butyldimethylsilyloxy-5-(4-fluorophenyl)hex-4-enoate (compound K-1, E configuration) according to the similar process as Example 15. $^1$H NMR (400 MHz, CDCl$_3$): δ 0.02 (s, 6H, 2×-CH$_3$), 0.88 (s, 9H, 3×-CH$_3$), 2.27-2.30 (m, 2H, —CH$_2$—), 2.35-2.39 (m, 2H, —CH$_2$—), 4.24 (s, 2H, —CH$_2$—), 5.71 (t, 1H, J=7.2 Hz, —CH—), 6.95-6.99 (m, 2H, Cpr-H), 7.32-7.36 (m, 2H, Cpr-H); MS (m/z): 361 [M+Na].

Example 17

Preparation of (4S)-3-[(Z)-6-tert-butyldimethylsilyloxy-5-(4-fluorophenyl)hex-4-enoyl]-4-phenyl-oxazolidin-2-one (Compound III-1, Z Configuration)

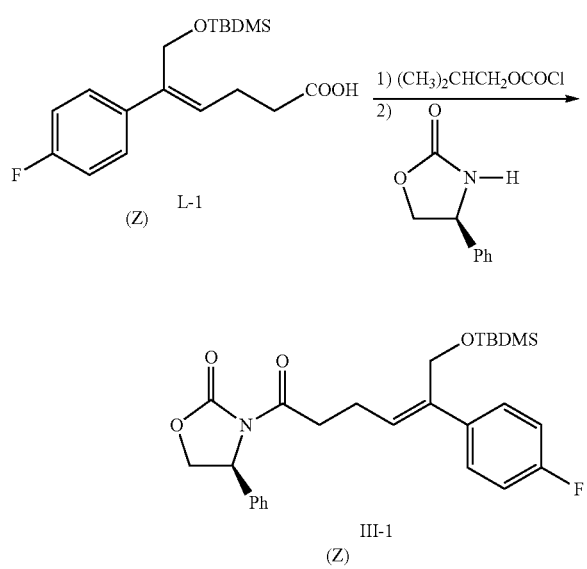

Step 1: To a 1 liter flask were added 39.21 grams (0.116 mol) compound L-1 (Z configuration), 300 ml of tetrahydrofuran and 19.0 ml (0.14 mol) of isobutyl chloroformate. Then, 19.3 ml (0.14 mol) of triethylamine was added dropwise therein at a temperature of about −60° C. After the addition, the mixture was warmed up to room temperature and the reaction lasted 30 minutes. The residue was filtered to obtain the mixed anhydride in tetrahydrofuran solution for further use.

Step 2: To a 3 liter flask were added 22.69 grams (0.14 mol) (S)-4-phenyl-2-oxazolidone and 0.6 liter of tetrahydrofuran. Then, 69.6 ml (2 mol/L) of sodium bis(trimethylsilyl)amide was added dropwise therein at about −25° C. The reaction lasted 30 minutes. Then, the tetrahydrofuran solution of mixed anhydride obtained from step 1 was added dropwise therein. After the addition, the mixture was warmed up to room temperature and the reaction lasted 1 hour. The residue was extracted 3 times with ethyl acetate (150 ml×3). The organic phases were combined, washed 3 times with brine, dried over anhydrous sodium sulfate and concentrated till dry to obtain 47.62 grams (0.10 mol) of compound III-1 (Z configuration), with the yield of 85%. $^1$H NMR (400 MHz, CDCl$_3$): δ 0.05 (s, 6H, 2×-CH$_3$), 0.86 (s, 9H, 3×-CH$_3$), 2.59-2.64 (m, 2H, —CH$_2$—), 3.13-3.18 (m, 2H, —CH$_2$—), 4.32-4.35 (m, 1H, —CH$_2$—), 4.50 (d, 1H, J=11.2 Hz, —CH$_2$—), 4.54 (d, 1H, J=13.3 Hz, —CH$_2$—), 4.74 (t, 1H, J=8.8 Hz, —CH$_2$—), 5.47-5.49 (m, 1H, —CH—), 5.74 (t, 1H, J=7.5 Hz, —CH—), 6.99-7.03 (m, 2H, Cpr-H), 7.31-7.41 (m, 7H, Cpr-H); MS (m/z): 506 [M+Na].

Example 18

Preparation of (4S)-3-[(E)-6-tert-butyldimethylsilyloxy-5-(4-fluorophenyl)hex-4-enoyl]-4-phenyl-oxazolidin-2-one (Compound III-1, E Configuration)

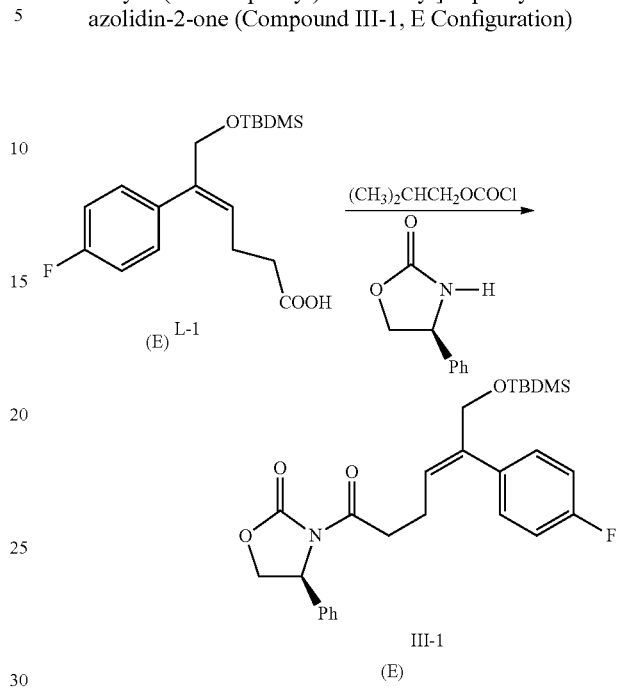

The title compound was prepared from (E)-6-tert-butyldimethylsilyloxy-5-(4-fluorophenyl)hex-4-enoic acid (compound L-1, E configuration) according to the similar process as Example 17. $^1$H NMR (400 MHz, CDCl$_3$): δ 0.01 (s, 6H, 2×-CH$_3$), 0.87 (s, 9H, 3×-CH$_3$), 2.23-2.28 (m, 2H, —CH$_2$—), 2.94-2.99 (m, 2H, —CH$_2$—), 4.22 (s, 2H, —CH$_2$—), 4.25-4.28 (m, 1H, —CH$_2$—), 4.66 (t, 1H, J=8.8 Hz, —CH$_2$—), 5.36-5.39 (m, 1H, —CH—), 5.69 (t, 1H, J=7.2 Hz, —CH—), 6.99-7.01 (m, 2H, Cpr-H), 7.06-7.08 (m, 2H, Cpr-H), 7.27-7.37 (m, 5H, Cpr-H); MS (m/z): 506 [M+Na].

Example 19

Preparation of [4-[(4-fluorophenyl)iminomethyl]phenyl]benzoate (Compound II-1)

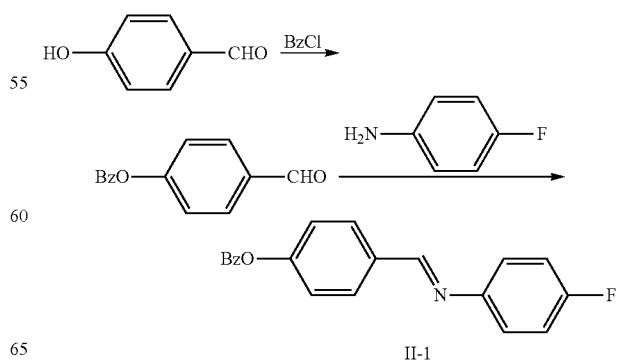

To a 500 ml flask were added 45.6 grams (0.374 mol) 4-hydroxylbenzaldehyde, 150 ml of acetone and 25.8 grams (0.187 mol) potassium carbonate. Then, 52.1 ml (0.449 mol) of benzoyl chloride (BzCl) was added therein dropwise slowly at a temperature of about 0° C. After the addition, the mixture was warmed up to room temperature and the reaction lasted 2 hours. The residue was extracted 3 times with ethyl acetate (150 ml×3). The organic phases were combined, dried over anhydrous sodium sulfate and concentrated till dry to obtain 76.08 grams (0.336 mol) 4-benzoyloxybenzaldehyde. Next, 35.7 ml (0.37 mol) of 4-fluoroaniline was added dropwise to a solution of the obtained 4-benzoyloxybenzaldehyde in 300 ml of ethyl acetate. The reaction lasted 1 hours. The reaction mixture was filtered. The obtained solid was recrystallized from anhydrous ethanol to obtain 60.3 grams (0.189 mol) white solid, namely compound II-1. $^1$H NMR (400 MHz, CDCl$_3$): δ 7.09-7.14 (m, 2H, Cpr-H), 7.23-7.28 (m, 2H, Cpr-H), 7.37-7.39 (m, 2H, Cpr-H), 7.54-7.59 (m, 2H, Cpr-H), 7.67-7.71 (m, 1H, Cpr-H), 7.99-8.02 (m, 2H, Cpr-H), 8.24-8.26 (m, 2H, Cpr-H), 8.49 (s, 1H, —CH—).

Example 20

Preparation of [4-[(Z,1S,2R)-6-tert-butyldimethylsilyloxy-1-(4-fluoroanilino)-5-(4-fluorophenyl)-2-[(4S)-2-oxo-4-phenyl-oxazolidine-3-carbonyl]hex-4-enyl]phenyl]benzoate (Compound IV-1, Z Configuration)

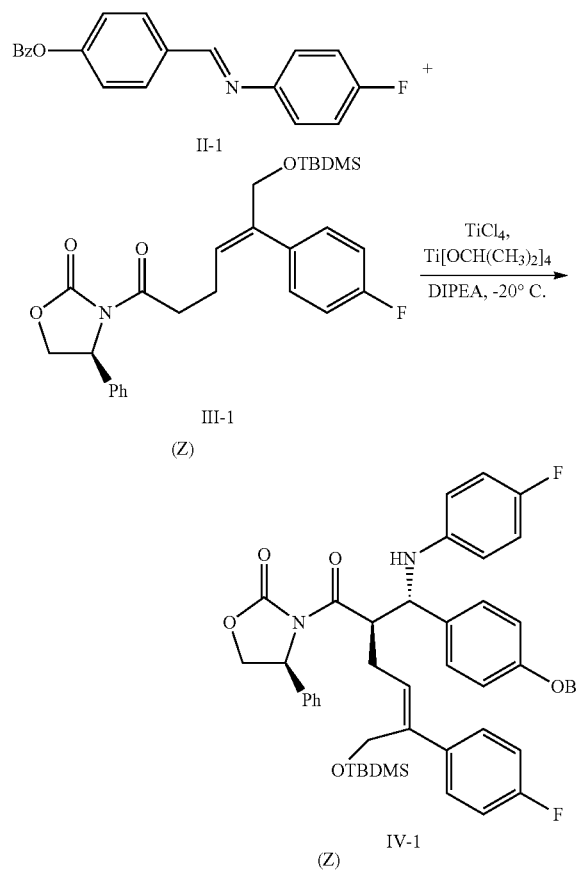

To a 1 liter flask were added 350 ml of dichloromethane and 20 grams powder molecular sieve under the protection of nitrogen, and further added 10.6 ml (95.7 mmol) of titanium tetrachloride and 9.6 ml (0.032 mol) of titanium tetra-isopropoxide at a temperature of about 0° C. After reacting for 15 minutes, 47.62 grams (98.6 mmol) compound III-1 (Z configuration) (dissolved in 60 ml of dichloromethane) was added. After reacting for 5 minutes, 37.8 ml (0.21 mol) of diisopropylethyl amine (DIPEA) was added at about 0° C. After reacting for 1 hour, the reaction solution was cooled to about −20° C., in which 34.97 grams (98.6 mmol) compound II-1 (dissolved in 0.87 liter of dichloromethane) was added. After reacting for 4 hours, 29 ml of acetic acid and 58 ml (2 mol/L) of sulfuric acid were added dropwise. The mixture was stirred at room temperature for 30 minutes, and then extracted 3 times with dichloromethane (120 ml×3). The organic phases were combined, dried over anhydrous sodium sulfate and concentrated until dry. The residue was purified by column chromatography to obtain 43.3 mmol compound IV-1 (Z configuration) with yield of 43.9%. $^1$H NMR (400 MHz, CDCl$_3$): δ 0.05 (s, 6H, 2×-CH$_3$), 0.86 (s, 9H, 3×-CH$_3$), 2.60-2.62 (m, 2H, —CH$_2$—), 3.15-3.16 (m, 1H, —CH—), 4.35-4.40 (m, 2H, —CH$_2$—), 4.46-4.52 (m, 2H, —CH$_2$—), 4.53-4.60 (m, 1H, —CH—), 4.72-4.76 (m, 1H, —NH—), 5.74 (t, 1H, J=7.2 Hz, —CH—), 6.80-6.85 (m, 1H, —CH—), 6.99-7.38 (m, 6H, Cpr-H), 7.39-7.41 (m, 8H, Cpr-H), 7.59-7.55 (m, 2H, Cpr-H), 7.69-7.72 (m, 1H, Cpr-H), 8.23-8.25 (m, 2H, Cpr-H); MS (m/z): 803 [M+H].

Example 21

Preparation of [4-[(E,1S,2R)-6-tert-butyldimethylsilyloxy-1-(4-fluoroanilino)-5-(4-fluorophenyl)-2-[(4S)-2-oxo-4-phenyl-oxazolidine-3-carbonyl]hex-4-enyl]phenyl]benzoate (Compound IV-1, E Configuration)

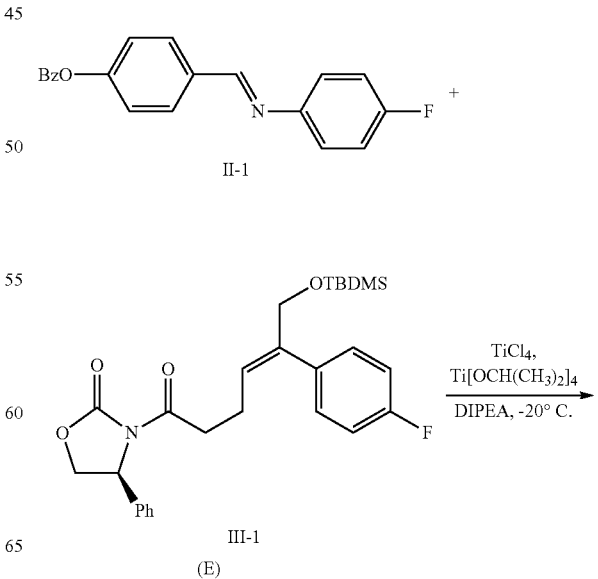

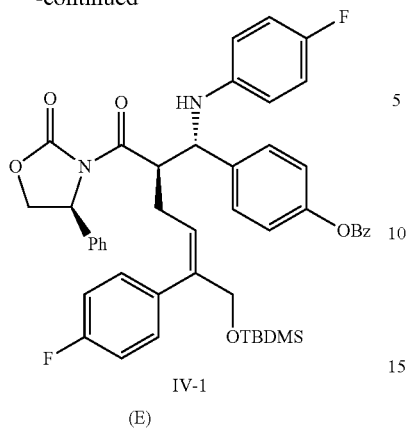

IV-1
(E)

The title compound was prepared from (4S)-3-[(E)-6-tert-butyldimethylsilyloxy-5-(4-fluorophenyl)hex-4-enoyl]-4-phenyl-ox azolidin-2-one (compound III-1, E configuration) according to the similar process as Example 20. ¹H NMR (400 MHz, CDCl₃): δ 0.01 (s, 6H, 2×-CH₃), 0.87 (s, 9H, 3×-CH₃), 2.24-2.26 (m, 2H, —CH₂—), 2.96-2.97 (m, 1H, —CH—), 4.28-4.33 (m, 2H, —CH₂—), 4.37-4.43 (m, 2H, —CH₂—), 4.51-4.58 (m, 1H, —CH—), 4.66-4.70 (m, 1H, —NH—), 5.68 (t, 1H, J=7.2 Hz, —CH—), 6.78-6.83 (m, 1H, —CH—), 6.88-7.25 (m, 6H, Cpr-H), 7.29-7.31 (m, 8H, Cpr-H), 7.52-7.54 (m, 2H, Cpr-H), 7.58-7.60 (m, 1H, Cpr-H), 8.15-8.17 (m, 2H, Cpr-H); MS (m/z): 803 [M+H].

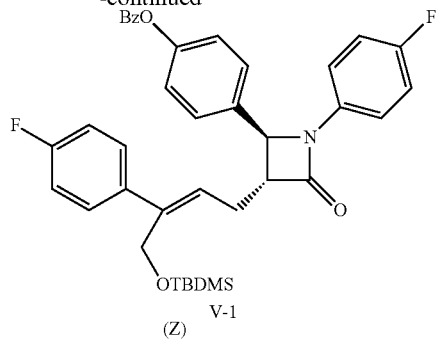

V-1
(Z)

To a 1 liter flask were added 42.5 mmol compound IV-1 (Z configuration), 350 ml of toluene and 22.93 grams (112.7 mmol) N,O-bis(trimethylsilyl)acetamide. The reaction lasted 1 hour at about 50° C. Then, 1.36 grams (4.3 mmol) tetrabutylammonium fluoride (TBAF) was added. The reaction was continued for 3 hours at the same temperature. After the reaction was completed, the heating was stopped. When the reaction system was cooled down to room temperature, the pH was adjusted to about 7.0 with 2 mol/L hydrochloric acid. The resultant was extracted with 300 ml of ethyl acetate, washed 3 times with brine, dried over anhydrous sodium sulfate, and concentrated till dry. The residue was purified by column chromatography to obtain 33.1 mmol compound V-1 (Z configuration) with yield of 77.9%. ¹H NMR (400 MHz, CDCl₃): δ 0.10 (s, 6H, 2×-CH₃), 0.90 (s, 9H, 3×-CH₃), 2.92-2.96 (m, 2H, —CH₂—), 3.31-3.32 (m, 1H, —CH—), 4.59 (d, 1H, J=12.0 Hz, —CH₂—), 4.71 (d, 1H, J=12.0 Hz, —CH₂—), 4.92 (d, 1H, J=2.3 Hz, —CH—), 5.78 (t, 1H, J=8.0 Hz, —CH—), 7.00-7.07 (m, 5H, Cpr-H), 7.26-7.38 (m, 5H, Cpr-H), 7.44-7.46 (m, 2H, Cpr-H), 7.56-7.60 (m, 2H, Cpr-H), 7.69-7.71 (m, 1H, Cpr-H), 8.24-8.26 (m, 2H, Cpr-H); MS (m/z): 640 [M+H].

Example 22

Preparation of (3R,4S)-4-(4-benzoyloxyphenyl)-1-(4-fluorophenyl)-3-[(Z)-3-(4-fluorophenyl)-4-tert-butyldimethylsilyloxy-but-2-enyl]azetidin-2-one (Compound V-1, Z Configuration)

Example 23

Preparation of (3R,4S)-4-(4-benzoyloxyphenyl)-1-(4-fluorophenyl)-3-[(E)-3-(4-fluorophenyl)-4-tert-butyldimethylsilyloxy-but-2-enyl]azetidin-2-one (Compound V-1, E Configuration)

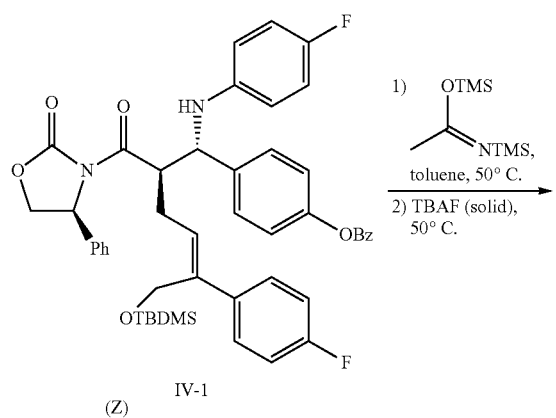

IV-1
(Z)

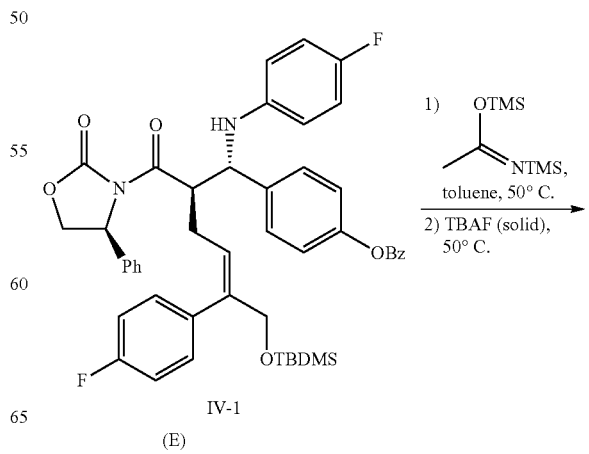

IV-1
(E)

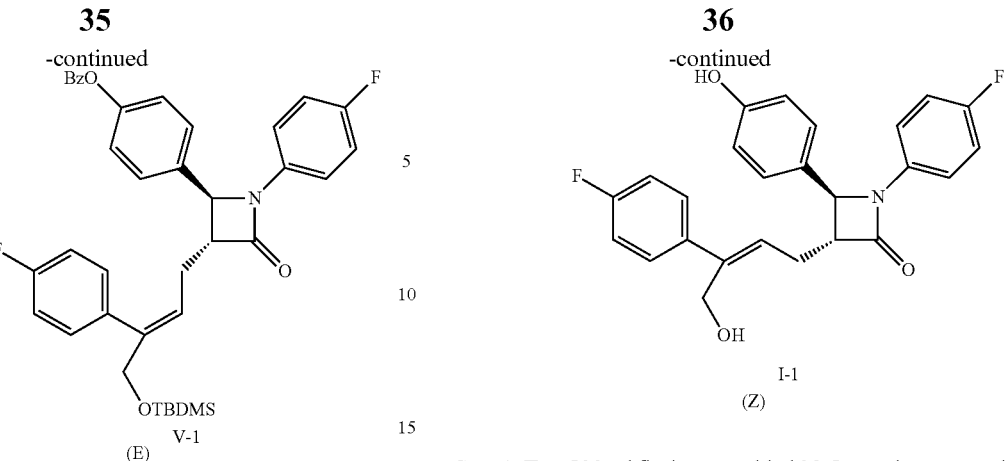

V-1 (E)

The title compound was prepared from [4-[(E,1S,2R)-6-tert-butyldimethylsilyloxy-1-(4-fluoroanilino)-5-(4-fluorophenyl)-2-[(4S)-2-oxo-4-phenyl-oxazolidine-3-carbonyl]hex-4-enyl]phenyl]benzoate (Compound IV-1, E Configuration) according to the similar process as Example 22. ¹H NMR (400 MHz, CDCl₃): δ 0.12 (s, 6H, 2×-CH₃), 0.93 (s, 9H, 3×-CH₃), 2.65-2.69 (m, 2H, —CH₂—), 3.09-3.10 (m, 1H, —CH—), 4.42 (d, 1H, J=12.0 Hz, —CH₂—), 4.54 (d, 1H, J=12.0 Hz, —CH₂—), 4.48 (d, 1H, J=2.3 Hz, —CH—), 5.71 (t, 1H, J=12.0 Hz, —CH—), 6.73-6.75 (m, 5H, Cpr-H), 6.92-6.98 (m, 5H, Cpr-H), 7.02-7.08 (m, 2H, Cpr-H), 7.22-7.25 (m, 5H, Cpr-H); MS (m/z): 640 [M+H].

Example 24

Preparation of (3R,4S)-1-(4-fluorophenyl)-3-[(Z)-3-(4-fluorophenyl)-4-hydroxy-but-2-enyl]-4-(4-hydroxyphenyl)azetidin-2-one (Compound I-1, Z Configuration)

Step 1: To a 500 ml flask were added 32.5 mmol compound V-1 (Z configuration), 250 ml of methanol and 4.89 grams (35.8 mmol) potassium carbonate. The mixture was stirred at room temperature, and the reaction lasted 30 minutes. After the reaction was completed, the residue was extracted 3 times with ethyl acetate (300 ml×3). The organic phases were combined, washed with brine, dried over anhydrous sodium sulfate and concentrated till dry for further use.

Step 2: The product of step 1 was dissolved in 200 ml of tetrahydrofuran. The pH was adjusted to about 1 with 6 mol/L hydrochloric acid. The mixture was stirred at room temperature, and the reaction last 30 minutes. The residue was extracted 3 times with ethyl acetate (250 ml×3). The organic phases were combined, washed with brine, dried over anhydrous sodium sulfate, concentrated till dry and purified by column chromatography to obtain 8.14 grams (19.3 mmol) compound I-1 (Z configuration) with yield of 59.4%. $[\alpha]^{24}_D = -1.67°$ (c=3 mg/ml MeOH), ¹H NMR (400 MHz, DMSO-d₆): δ 2.72-2.84 (m, 2H, —CH₂—), 3.20-3.25 (m, 1H, —CH—), 4.39 (d, 2H, J=5.2 Hz, —CH₂—), 4.85 (t, 1H, J=5.2 Hz, —OH), 4.93 (d, 1H, J=2.3 Hz, —CH—), 5.80 (t, 1H, J=7.6 Hz, —CH—), 6.73-6.76 (m, 2H, Cpr-H), 7.10-7.20 (m, 4H, Cpr-H), 7.21-7.39 (m, 4H, Cpr-H), 8.40-7.42 (m, 2H, Cpr-H), 9.48 (s, 1H, —OH); MS (m/z): 422 [M+H].

Example 25

Preparation of (3R,4S)-1-(4-fluorophenyl)-3-[(E)-3-(4-fluorophenyl)-4-hydroxy-but-2-enyl]-4-(4-hydroxyphenyl)azetidin-2-one (Compound I-1, E Configuration)

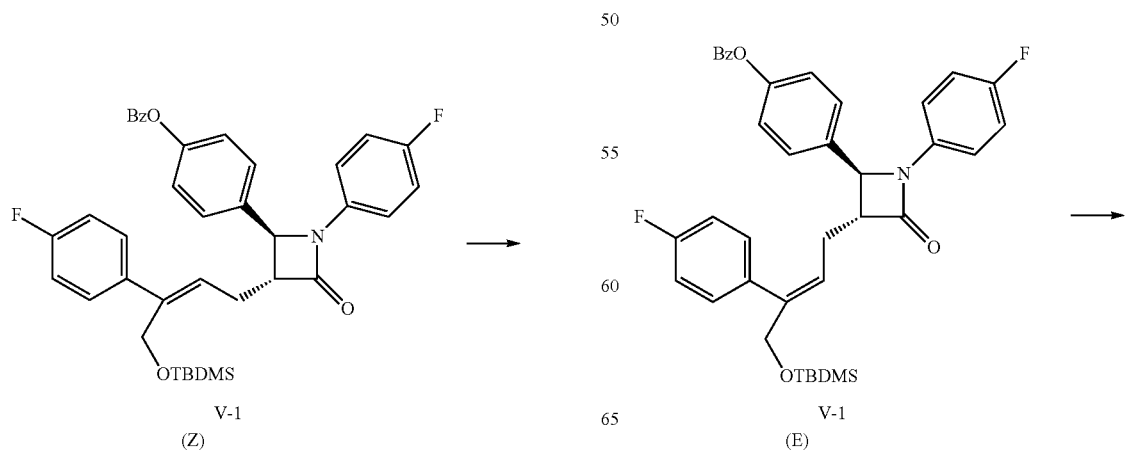

-continued

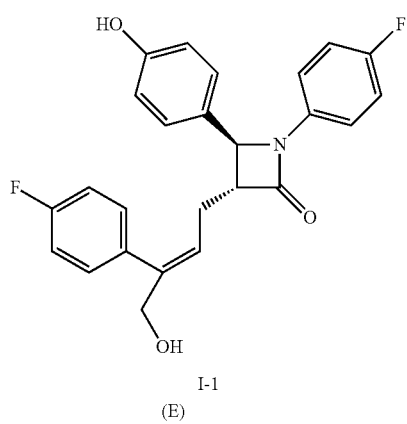

I-1
(E)

The title compound was prepared from (3R,4S)-4-(4-benzoyloxyphenyl)-1-(4-fluorophenyl)-3-[(E)-3-(4-fluorophenyl)-4-tert-butyldimethylsilyloxy-but-2-enyl]azetidin-2-one (compound V-1 E configuration) according to the similar process as Example 24. $^1$H NMR (400 MHz, CDCl$_3$): δ 2.45-2.57 (m, 2H, —CH$_2$—), 2.98-3.02 (m, 1H, —CH—), 4.22 (s, 2H, —CH$_2$—), 4.41 (d, 1H, J=2.3 Hz, —CH—), 5.73 (t, 1H, J=7.2 Hz, —CH—), 6.75-6.77 (m, 2H, Cpr-H), 6.82-6.86 (m, 2H, Cpr-H), 6.98-7.00 (m, 2H, Cpr-H), 7.04-7.07 (m, 2H, Cpr-H), 7.09-7.19 (m, 4H, Cpr-H); MS (m/z): 422 [M+H].

The following compound is prepared by using the similar method and proper starting materials.

| Examples | Compounds | $^1$H NMR (400 MHz) | MS (m/z): |
|---|---|---|---|
| 26 | 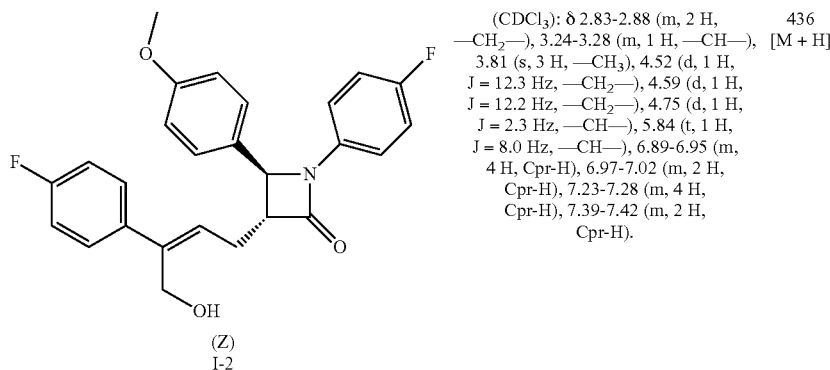<br>(Z)<br>I-2 | (CDCl$_3$): δ 2.83-2.88 (m, 2 H, —CH$_2$—), 3.24-3.28 (m, 1 H, —CH—), 3.81 (s, 3 H, —CH$_3$), 4.52 (d, 1 H, J = 12.3 Hz, —CH$_2$—), 4.59 (d, 1 H, J = 12.2 Hz, —CH$_2$—), 4.75 (d, 1 H, J = 2.3 Hz, —CH—), 5.84 (t, 1 H, J = 8.0 Hz, —CH—), 6.89-6.95 (m, 4 H, Cpr-H), 6.97-7.02 (m, 2 H, Cpr-H), 7.23-7.28 (m, 4 H, Cpr-H), 7.39-7.42 (m, 2 H, Cpr-H). | 436 [M + H] |
| 27 | 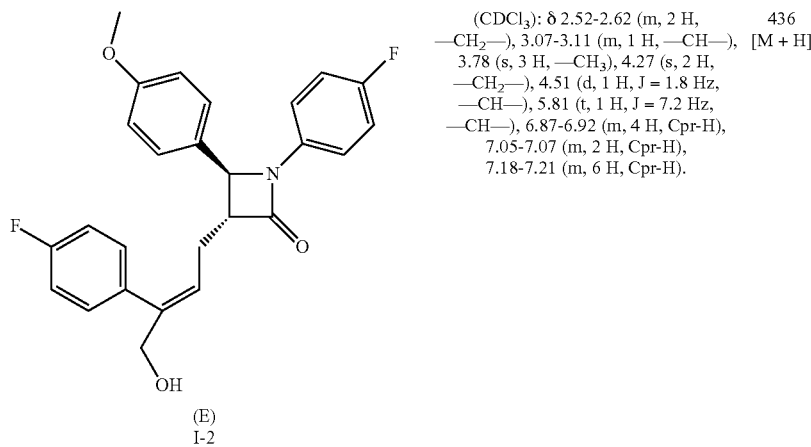<br>(E)<br>I-2 | (CDCl$_3$): δ 2.52-2.62 (m, 2 H, —CH$_2$—), 3.07-3.11 (m, 1 H, —CH—), 3.78 (s, 3 H, —CH$_3$), 4.27 (s, 2 H, —CH$_2$—), 4.51 (d, 1 H, J = 1.8 Hz, —CH—), 5.81 (t, 1 H, J = 7.2 Hz, —CH—), 6.87-6.92 (m, 4 H, Cpr-H), 7.05-7.07 (m, 2 H, Cpr-H), 7.18-7.21 (m, 6 H, Cpr-H). | 436 [M + H] |

| Examples | Compounds | ¹H NMR (400 MHz) | MS (m/z): |
|---|---|---|---|
| 28 | 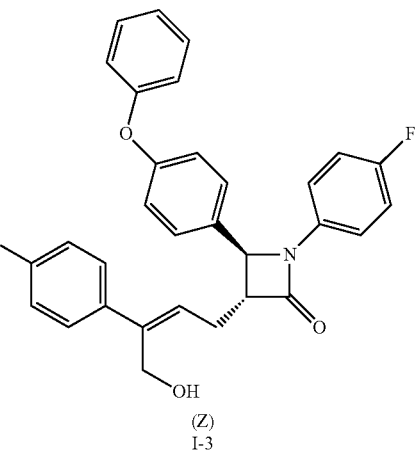<br>(Z)<br>I-3 | (CDCl₃): δ 2.85-2.89 (m, 2 H, —CH₂—), 3.26-3.30 (m, 1 H, —CH—), 4.52 (d, 1 H, J = 12.3 Hz, —CH₂—), 4.59 (d, 1 H, J = 12.3 Hz, —CH₂—), 4.78 (d, 1 H, J = 2.3 Hz, —CH—), 5.85 (t, 1 H, J = 8.0 Hz, —CH—), 6.93-7.04 (m, 8 H, Cpr-H), 7.12-7.16 (m, 1 H, Cpr-H), 7.24-7.31 (m, 4 H, Cpr-H), 7.33-7.42 (m, 4 H, Cpr-H). | 498 [M + H] |
| 29 | 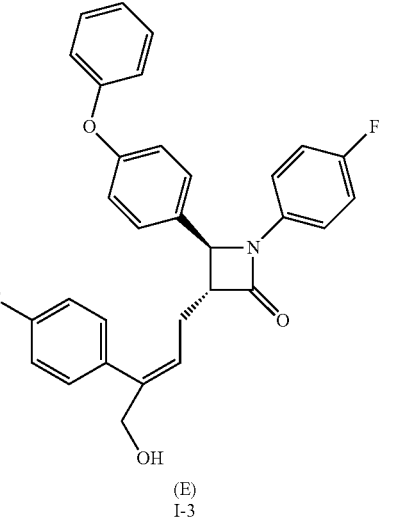<br>(E)<br>I-3 | (CDCl₃): δ 2.54-2.66 (m, 2 H, —CH₂—), 3.10-3.14 (m, 1 H, —CH—), 4.31 (s, 2 H, —CH₂—), 4.52 (d, 1 H, J = 2.3 Hz, —CH—), 5.83 (t, 1 H, J = 7.2 Hz, —CH—), 6.91-7.03 (m, 6 H, Cpr-H), 7.04-7.10 (m, 2 H, Cpr-H), 7.12-7.16 (m, 1 H, Cpr-H), 7.18-7.24 (m, 6 H, Cpr-H), 7.33-7.38 (m, 2 H, Cpr-H). | 498 [M + H] |
| 30 | 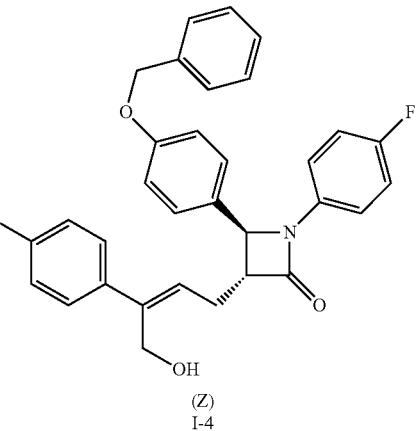<br>(Z)<br>I-4 | (CDCl₃): δ 2.83-2.87 (m, 2 H, —CH₂—), 3.24-3.28 (m, 1 H, —CH—), 4.51 (d, 1 H, J = 12.2 Hz, —CH₂—), 4.58 (d, 1 H, J = 12.3 Hz, —CH₂—), 4.74 (d, 1 H, J = 2.2 Hz, —CH—), 5.05 (s, 2 H, —CH₂—), 5.83 (t, 1 H, J = 8.0 Hz, —CH—), 6.90-7.01 (m, 6 H, Cpr-H), 7.23-7.28 (m, 4 H, Cpr-H), 7.33-7.43 (m, 7 H, Cpr-H); | 512 [M + H] |

-continued

| Examples | Compounds | $^1$H NMR (400 MHz) | MS (m/z): |
|---|---|---|---|
| 31 | (E) I-4 | (CDCl$_3$): δ 2.51-2.64 (m, 2 H, —CH$_2$—), 3.07-3.11 (m, 1 H, —CH—), 4.29 (s, 2 H, —CH$_2$—), 4.49 (d, 1 H, J = 2.3 Hz, —CH—), 5.04 (s, 2 H, —CH$_2$—), 5.81 (t, 1 H, J = 7.2 Hz, —CH—), 6.88-7.00 (m, 4 H, Cpr-H), 7.03-7.09 (m, 2 H, Cpr-H), 7.17-7.23 (m, 6 H, Cpr-H), 7.31-7.43 (m, 5 H, Cpr-H); | 512 [M + H] |

Example 32

Preparation of (3R,4S)-4-(4-benzoyloxyphenyl)-1-(4-fluorophenyl)-3-[(Z)-3-(4-fluorophenyl)-4-hydroxy-but-2-enyl]azetidin-2-one (Compound I-5, Z Configuration)

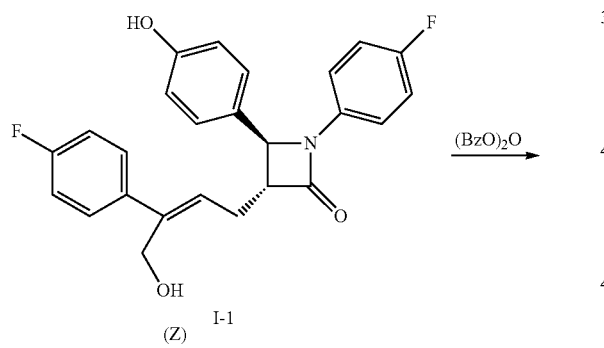

To a 250 ml flask were added 19.0 mmol compound I-1 (Z configuration), 100 ml of dichloromethane, 4.72 grams (20.9 mmol) benzoic anhydride and 3.3 ml of triethylamine. The mixture was stirred at room temperature, and the reaction lasted 2 hours. After the reaction was completed, the residue was extracted 3 times with ethyl acetate (100 ml×3). The organic phases were combined, washed with brine, dried over anhydrous sodium sulfate and concentrated till dry. The residue was purified by column chromatography to obtain 8.04 grams (15.3 mmol) compound I-5 (Z configuration) with yield of 80.6%. $^1$H NMR (400 MHz, CDCl$_3$): δ 2.87-2.91 (m, 2H, —CH$_2$—), 3.29-3.34 (m, 1H, —CH—), 4.54 (d, 1H, J=12.3 Hz, —CH$_2$—), 4.60 (d, 1H, J=12.2 Hz, —CH$_2$—), 4.85 (d, 1H, J=2.2 Hz, —CH—), 5.86 (t, 1H, J=8.0 Hz, —CH—), 6.94-7.04 (m, 4H, Cpr-H), 7.24-7.29 (m, 4H, Cpr-H), 7.39-7.43 (m, 4H, Cpr-H), 7.50-7.54 (m, 2H, Cpr-H), 7.64-7.68 (m, 1H, Cpr-H), 8.18-8.20 (m, 2H, Cpr-H); MS (m/z): 526 [M+H].

Example 33

Preparation of (3R,4S)-4-(4-acetoxyphenyl)-1-(4-fluorophenyl)-3-[(Z)-3-(4-fluorophenyl)-4-hydroxy-but-2-enyl]azetidin-2-one (I-6 Z Configuration)

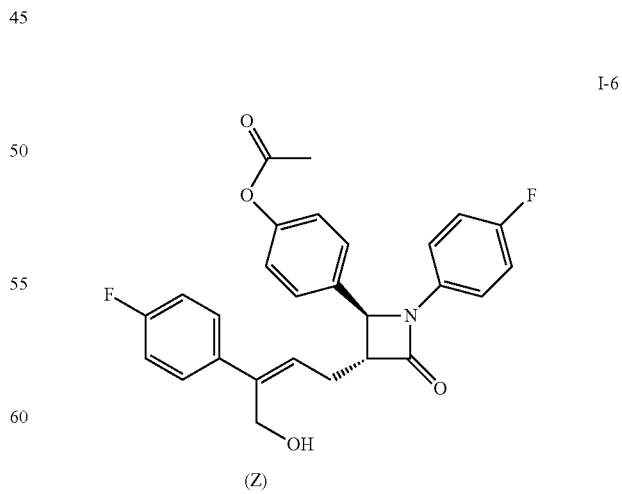

Compound I-1 (Z configuration) was used as starting material, and compound I-6 (Z configuration) was prepared according to the process of Example 32. $^1$H NMR (400 MHz, CDCl₃): δ 2.30 (s, 3H, —CH₃), 2.83-2.88 (m, 2H, —CH₂—), 3.24-3.29 (m, 1H, —CH—), 4.51 (d, 1H, J=12.2 Hz, —CH₂—), 4.58 (d, 1H, J=12.3 Hz, —CH₂—), 4.81 (d, 1H, J=2.4 Hz, —CH—), 5.82 (t, 1H, J=8.0 Hz, —CH—), 6.91-7.01 (m, 4H, Cpr-H), 7.09-7.12 (m, 2H, Cpr-H), 7.22-7.26 (m, 2H, Cpr-H), 7.34-7.38 (m, 2H, Cpr-H), 7.38-7.41 (m, 2H, Cpr-H); MS (m/z): 464 [M+H].

Example 34

Preparation of (3R,4S)-4-(4-benzoyloxyphenyl)-1-(4-fluorophenyl)-3-[(Z)-3-(4-fluorophenyl)-4-hydroxy-pent-2-enyl]azetidin-2-one (Compound I-7, Z Configuration)

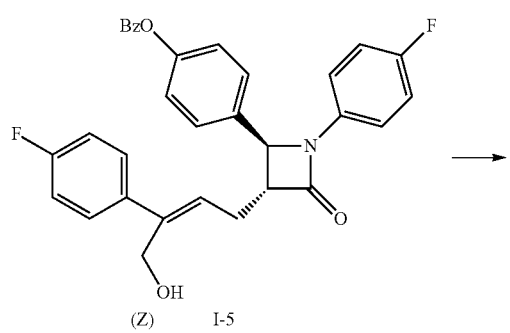

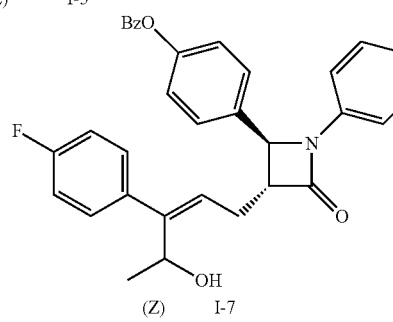

Step 1: To a 100 ml flask were added 15.0 mmol compound I-5 (Z configuration), 20 ml of dichloromethane and 7.63 grams (18.0 mmol) Dess-Martin periodinane. The mixture was stirred at room temperature and the reaction lasted 2 hours. After the reaction was completed, the resultant was washed with ether. The filtrate was concentrated till dry and directly used in the next step without further purification.

Step 2: To a 100 ml flask were added 18.0 mmol methyl magnesium chloride and 30 ml of anhydrous tetrahydrofuran. The mixture was cooled to −10° C., in which the tetrahydrofuran solution of product of step 1 was added dropwise slowly. After the addition, the mixture was warmed up to 0° C. and the reaction lasted 2 hours. After the reaction was completed, the residue was neutralized with saturated NH₄Cl solution and extracted 3 times with dichloromethane (80 ml×3). The organic phases were combined, washed with brine, dried over anhydrous sodium sulfate and concentrated till dry. The residue was purified by column chromatography to obtain 2.29 grams (4.25 mmol) compound I-7 (Z configuration) with yield of 52.6%. ¹H NMR (400 MHz, CDCl₃): δ 1.26 (d, 3H, —CH₃), 2.80-2.98 (m, 2H, —CH₂—), 3.32-3.35 (m, 1H, —CH—), 4.80 (d, 1H, —CH—), 5.03-5.08 (m, 1H, —CH—), 5.52-5.59 (m, 1H, —CH—), 6.93-7.00 (m, 4H, Cpr-H), 7.23-7.32 (m, 6H, Cpr-H), 7.38-7.47 (m, 2H, Cpr-H), 7.50-7.54 (m, 2H, Cpr-H), 7.64-7.67 (m, 1H, Cpr-H), 8.15-8.20 (m, 2H, Cpr-H); MS (m/z): 584 [M−H+HCOOH].

Example 35

Preparation of (3R,4S)-1-(4-fluorophenyl)-3-[(Z)-3-(4-fluorophenyl)-4-hydroxy-pent-2-enyl]-4-(4-hydroxyphenyl)azetidin-2-one (Compound I-8, Z Configuration)

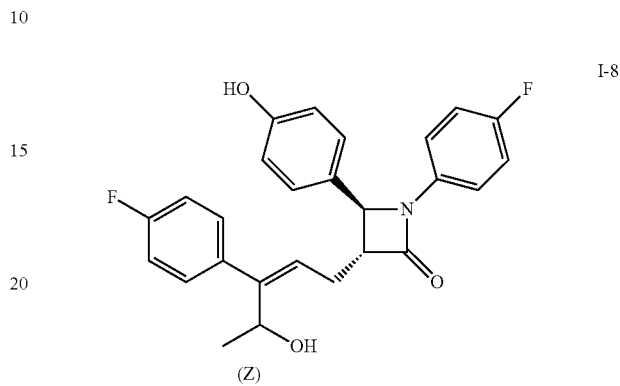

The compound I-7 (Z configuration) was used as starting material, and according to step 1 of Example 24, the benzoyl protecting group was removed to obtain compound I-8 (Z configuration). ¹H NMR (400 MHz, DMSO-d₆): δ 1.11 (d, 3H, —CH₃), 2.76-2.83 (m, 2H, —CH₂—), 3.20-3.24 (m, 1H, —CH—), 4.91-4.93 (m, 2H, 2×-CH—), 4.93 (s, 1H, —OH), 5.45 (t, 1H, J=7.2 Hz, —CH—), 6.74-6.78 (m, 2H, Cpr-H), 7.07-7.19 (m, 4H, Cpr-H), 7.21-7.26 (m, 4H, Cpr-H), 7.33-7.39 (m, 2H, Cpr-H), 9.56 (s, 1H, —OH); MS (m/z): 434 [M−H].

Example 36

Preparation of (3R,4S)-1-(4-fluorophenyl)-3-[(E)-3-(4-fluorophenyl)-4-hydroxy-pent-2-enyl]-4-(4-hydroxyphenyl)azetidin-2-one (Compound I-8, E Configuration)

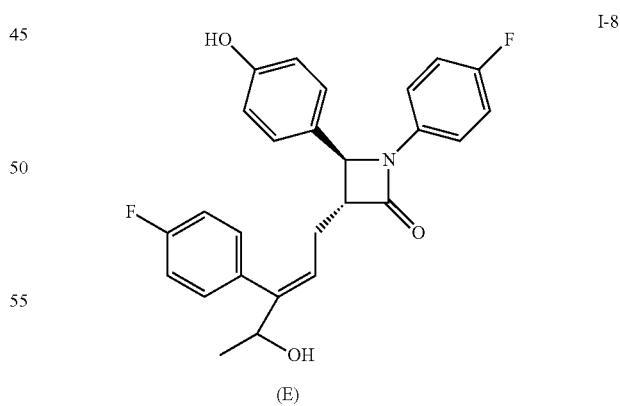

The compound I-1 (E configuration) was used as starting material, and compound I-8 (E configuration) was prepared according to the processes of Example 32, Example 34 and Example 35 sequentially. ¹H NMR (400 MHz, CDCl₃): δ 1.18 (d, 3H, —CH₃), 2.43-2.50 (m, 2H, —CH₂—), 3.04-3.06 (m, 1H, —CH—), 4.48-4.50 (m, 2H, 2×-CH—), 5.78 (t, 1H, J=7.2 Hz, —CH—), 6.82-6.85 (m, 2H, Cpr-H), 6.89-6.94 (m, 2H, Cpr-H), 7.02-7.07 (m, 2H, Cpr-H), 7.12-7.15 (m, 4H, Cpr-H), 7.18-7.22 (m, 2H, Cpr-H); MS (m/z): 434 [M−H].

Example 37

Preparation of (3R,4S)-4-(4-benzoyloxyphenyl)-1-(4-fluorophenyl)-3-[(Z)-3-(4-fluorophenyl)-4-hydroxy-4-methyl-pent-2-enyl]azetidin-2-one (Compound I-9, Z Configuration)

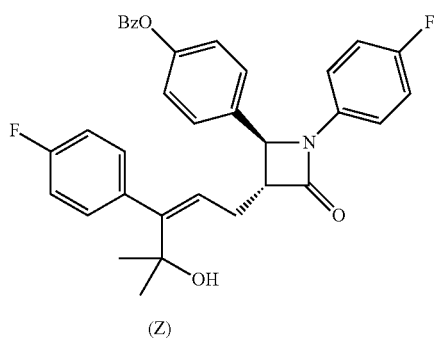

The compound I-7 (Z configuration) was used as starting material, and compound I-9 (Z configuration) was prepared according to the processes of step 1 and step 2 in Example 34. $^1$H NMR (400 MHz, CDCl$_3$): δ 1.35 (s, 3H, —CH$_3$), 1.38 (s, 3H, —CH$_3$), 3.01-3.09 (m, 1H, —CH—), 3.26-3.34 (m, 2H, —CH$_2$—), 4.86 (s, 1H, —CH—), 5.34 (t, 1H, J=7.6 Hz, —CH—), 6.89-7.04 (m, 6H, Cpr-H), 7.23-7.30 (m, 4H, Cpr-H), 7.39-7.41 (m, 2H, Cpr-H), 7.50-7.54 (m, 2H, Cpr-H), 7.64-7.65 (m, 1H, Cpr-H), 8.18-8.20 (m, 2H, Cpr-H); MS (m/z): 598 [M−H+HCOOH].

Example 38

Preparation of (3R,4S)-1-(4-fluorophenyl)-3-[(Z)-3-(4-fluorophenyl)-4-hydroxy-4-methyl-pent-2-enyl]-4-(4-hydroxyphenyl)azetidin-2-one (Compound I-10, Z Configuration)

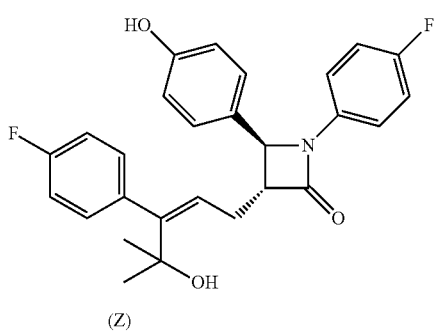

The compound I-9 (Z configuration) was used as starting material, and according to the process of step 1 in Example 24, the benzoyl protecting group was removed to obtain compound I-10 (Z configuration). $^1$H NMR (400 MHz, DMSO-d$_6$): δ 1.21 (s, 3H, —CH$_3$), 1.23 (s, 3H, —CH$_3$), 2.96-3.08 (m, 2H, —CH$_2$—), 3.16-3.20 (m, 1H, —CH—), 4.88 (s, 1H, —CH—), 4.96 (s, 1H, —OH), 5.14 (t, 1H, J=7.6 Hz, —CH—), 6.74-6.76 (m, 2H, Cpr-H), 7.06-7.07 (m, 4H, Cpr-H), 7.12-7.16 (m, 4H, Cpr-H), 7.19-7.23 (m, 4H, Cpr-H), 9.51 (s, 1H, —OH); MS (m/z): 448 [M−H].

Example 39

Preparation of (3R,4S)-3-[(Z)-4-acetoxy-3-(4-fluorophenyl)-but-2-enyl]-4-(4-acetoxyphenyl)-1-(4-fluorophenyl)azetidin-2-one (Compound I-11, Z Configuration)

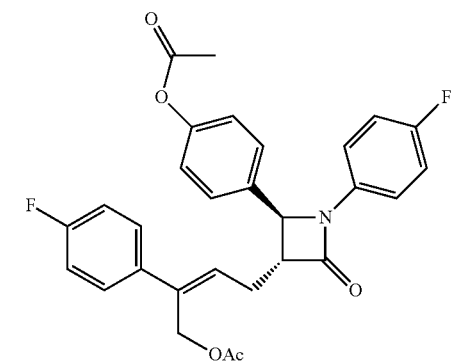

To a 250 ml flask were added 19.0 mmol compound I-1 (Z configuration), 100 ml of dichloromethane, 4.84 grams (47.5 mmol) acetic anhydride and 7.5 ml of triethylamine. The mixture was stirred at room temperature, and the reaction lasted 2 hours. After the reaction was completed, the residue was extracted 3 times with ethyl acetate (100 ml×3). The organic phases were combined, washed with brine, dried over anhydrous sodium sulfate and concentrated till dry. The residue was purified by column chromatography to obtain 8.16 grams (16.2 mmol) compound I-11 (Z configuration) with yield of 85.0%. $^1$H NMR (400 MHz, CDCl$_3$): δ 2.00 (s, 3H, —CH$_3$), 2.30 (s, 3H, —CH$_3$), 2.88-2.92 (m, 2H, —CH$_2$—), 3.23-3.27 (m, 1H, —CH—), 4.76 (d, 1H, J=2.2 Hz, —CH—), 5.03 (d, 1H, J=12.9 Hz, —CH$_2$—), 5.06 (d, 1H, J=12.9 Hz, —CH$_2$—), 5.95 (t, 1H, J=7.6 Hz, —CH—), 6.93-6.98 (m, 2H, Cpr-H), 6.98-7.03 (m, 2H, Cpr-H), 7.09-7.11 (m, 2H, Cpr-H), 7.23-7.29 (m, 4H, Cpr-H), 7.30-7.34 (m, 2H, Cpr-H); MS (m/z): 506 [M+H].

Example 40

Preparation of (3R,4S)-3-[(Z)-4-acetoxy-3-(4-fluorophenyl)-but-2-enyl]-1-(4-fluorophenyl)-4-(4-hydroxyphenyl)azetidin-2-one (Compound I-12, Z Configuration)

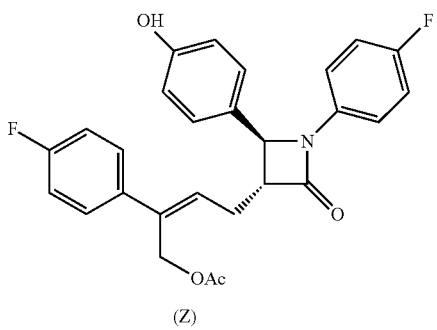

The compound I-11 (Z configuration) was used as starting material, and according to the process of step 1 in Example 24, the acetyl protection group was removed from phenolic hydroxyl to obtain compound I-12 (Z configuration). ¹H NMR (400 MHz, DMSO-d₆): δ 1.94 (s, 3H, —CH₃), 2.76-2.88 (m, 2H, —CH₂—), 3.23-3.27 (m, 1H, —CH—), 4.90 (d, 1H, —CH—), 5.03 (d, 1H, J=12.8 Hz, —CH₂—), 5.07 (d, 1H, J=12.8 Hz, —CH₂—), 6.01 (t, 1H, J=7.6 Hz, —CH—), 6.74-6.76 (m, 2H, Cpr-H), 7.12-7.21 (m, 6H, Cpr-H), 7.21-7.25 (m, 2H, Cpr-H), 7.36-7.40 (m, 2H, Cpr-H), 9.52 (s, 1H, —OH); MS (m/z): 464 [M+H].

The following compounds were prepared by using proper starting materials according to processes of Example 39 and Example 40.

| Examples | Compounds | ¹H NMR (400 MHz) | MS (m/z): |
|---|---|---|---|
| 41 | 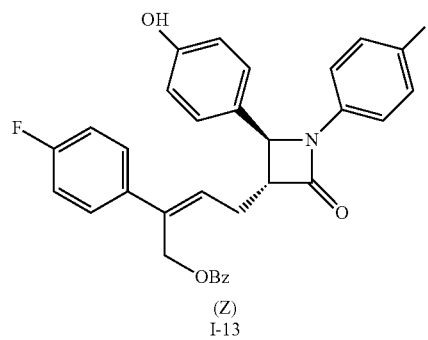<br>(Z)<br>I-13 | (DMSO-d₆): δ 2.83-2.96 (m, 2 H, —CH₂—), 3.26-3.33 (m, 1 H, —CH—), 4.91 (d, 1 H, —CH—), 5.34 (s, 2 H, —CH₂—), 6.09 (t, 1 H, J = 8.0 Hz, —CH—), 6.72-6.74 (m, 2 H, Cpr-H), 7.11-7.21 (m, 8 H, Cpr-H), 7.44-7.49 (m, 4 H, Cpr-H), 7.60-7.64 (m, 1 H, Cpr-H), 7.79-7.82 (m, 2 H, Cpr-H), 9.52 (s, 1 H, —OH). | 526 [M + H] |
| 42 | 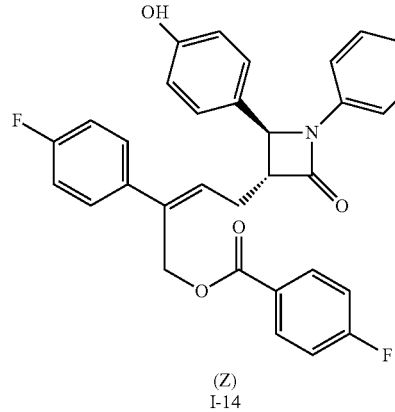<br>(Z)<br>I-14 | (DMSO-d₆): δ 2.83-2.96 (m, 2 H, —CH₂—), 3.26-3.35 (m, 1 H, —CH—), 4.91 (d, 1 H, J = 2.2 Hz, —CH—), 5.34 (s, 2 H, —CH₂—), 6.10 (t, 1 H, J = 7.6 Hz, —CH—), 6.72-6.74 (m, 2 H, Cpr-H), 7.12-7.22 (m, 8 H, Cpr-H), 7.28-7.33 (m, 2 H, Cpr-H), 7.44-7.48 (m, 2 H, Cpr-H), 7.84-7.88 (m, 2 H, Cpr-H), 9.54 (s, 1 H, —OH). | 544 [M + H] |
| 43 | 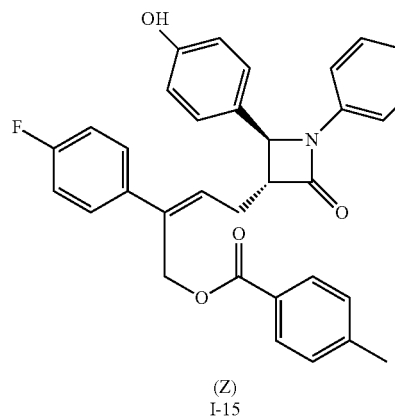<br>(Z)<br>I-15 | Z: (DMSO-d₆): δ 2.18-2.26 (m, 1 H, —CH₂—), 2.29 (s, 3 H, —CH₃), 2.33-2.46 (m, 1 H, —CH₂—), 3.79-3.85 (m, 1 H, —CH—), 4.80 (d, 1 H, J = 12.7 Hz, —CH₂—), 4.84 (d, 1 H, J = 13.0 Hz, —CH₂—), 5.34 (d, 1 H, —CH—), 5.77 (t, 1 H, J = 7.2 Hz, —CH—), 6.74-6.77 (m, 2 H, Cpr-H), 7.11-7.19 (m, 6 H, Cpr-H), 7.23-7.28 (m, 4 H, Cpr-H), 7.36-7.39 (m, 2 H, Cpr-H), 7.65-7.67 (m, 2 H, Cpr-H), 9.54 (s, 1 H, —OH). | 540 [M + H] |

Example 44

(3R,4S)-3-[(Z)-4-acetoxy-3-(4-fluorophenyl)-but-2-enyl]-4-(4-benzoyloxyphenyl)-1-(4-fluorophenyl)azetidin-2-one (Compound I-16, Z Configuration)

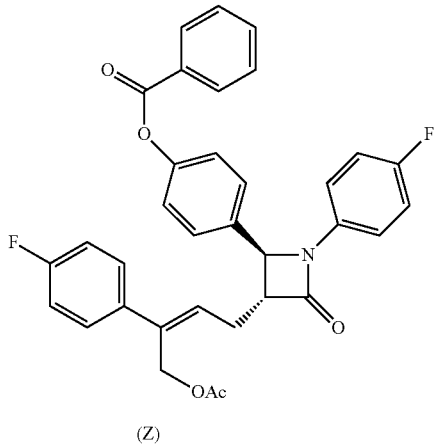

(Z)

To a 250 ml flask were added 16.0 mmol compound I-5 (Z configuration), 100 ml of dichloromethane, 1.96 grams (19.2 mmol) acetic anhydride and 2.8 ml of triethylamine. The mixture was stirred at room temperature, and the reaction lasted 2 hours. After the reaction was completed, the residue was extracted 3 times with ethyl acetate (100 ml×3). The organic phases were combined, washed with brine, dried over anhydrous sodium sulfate and concentrated until dry. The residue was purified by column chromatography to obtain 7.94 grams (14.0 mmol) compound I-16 (Z configuration) with yield of 87.5%. $^1$H NMR (400 MHz, CDCl$_3$): δ 2.00 (s, 3H, —CH$_3$), 2.90-2.94 (m, 2H, —CH$_2$—), 3.27-3.31 (m, 1H, —CH—), 4.80 (d, 1H, J=2.3 Hz, —CH—), 5.04 (d, 1H, J=12.2 Hz, —CH$_2$—), 5.08 (d, 1H, J=13.2 Hz, —CH$_2$—), 5.97 (t, 1H, J=8.0 Hz, —CH—), 6.95-7.03 (m, 4H, Cpr-H), 7.23-7.32 (m, 6H, Cpr-H), 7.38-7.40 (m, 2H, Cpr-H), 7.50-7.54 (m, 2H, Cpr-H), 7.63-7.67 (m, 1H, Cpr-H), 8.18-8.20 (m, 2H, Cpr-H); MS (m/z): 568 [M+H].

Example 45

(3R,4S)-3-[(Z)-4-acetoxy-3-(4-fluorophenyl)-but-2-enyl]-1-(4-fluorophenyl)-4-(4-methoxyphenyl)azetidin-2-one (Compound I-17, Z Configuration)

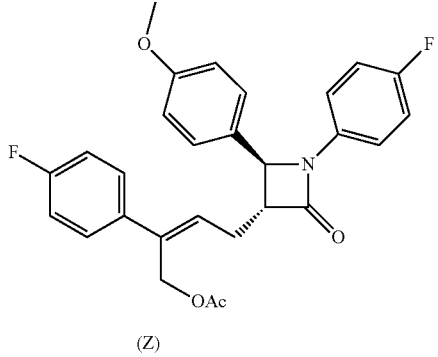

(Z)

Compound I-17 (Z configuration) was prepared according to the process of Example 44 by using compound I-2 (Z configuration) as starting material. $^1$H NMR (400 MHz, CDCl$_3$): δ 1.99 (s, 3H, —CH$_3$), 2.87-2.91 (m, 2H, —CH$_2$—), 3.21-3.25 (m, 1H, —CH—), 3.80 (s, 3H, —CH$_3$), 4.70 (d, 1H, J=2.2 Hz, —CH—), 5.04 (s, 2H, —CH$_2$—), 5.96 (t, 1H, J=7.6 Hz, —CH—), 6.88-6.96 (m, 4H, Cpr-H), 6.98-7.02 (m, 2H, Cpr-H), 7.23-7.31 (m, 6H, Cpr-H); MS (m/z): 500 [M+Na].

Example 46

(3R,4S)-3-[(E)-4-acetoxy-3-(4-fluorophenyl)-but-2-enyl]-1-(4-fluorophenyl)-4-(4-methoxyphenyl)azetidin-2-one (Compound I-17, E Configuration)

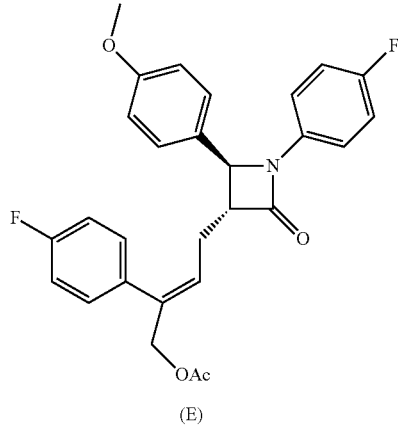

(E)

Compound I-17 (E configuration) was prepared according to the process of Example 44 by using compound I-2 (E configuration) as starting material. $^1$H NMR (400 MHz, CDCl$_3$): δ 1.96 (s, 3H, —CH$_3$), 2.52-2.67 (m, 2H, —CH$_2$—), 3.07-3.11 (m, 1H, —CH—), 3.80 (s, 3H, —CH$_3$), 4.47 (d, 1H, J=2.3 Hz, —CH—), 4.72 (d, 1H, J=13.0 Hz, —CH$_2$—), 4.77 (d, 1H, J=13.0 Hz, —CH$_2$—), 5.80 (t, 1H, J=7.6 Hz, —CH—), 6.87-6.94 (m, 4H, Cpr-H), 7.05-7.09 (m, 2H, Cpr-H), 7.16-7.23 (m, 6H, Cpr-H); MS (m/z): 500 [M+Na].

In Vivo Pharmacodynamic Screening

The in vivo pharmacodynamic screening of the compound of the present invention was performed by the following processes.

1. Establishment of Hypercholesterolemia Model of Golden Hamster:

The animals were subjected to acclimation feeding for 1 week with free feeding and drinking under a lighting condition of 10 h/14 h. On Day 8, the animals were raised with high fat feed (consisting of 0.5% cholesterol, 20% palm oil, 79.5% basal feed) for 1 week. Then, each animal was anesthetized by ether. After weighing, 0.5 ml blood was obtained from orbital vein, anticoagulated with heparin and centrifuged at 5000 rpm for 10 min. The plasma was collected and the levels of plasma TC (total cholesterol) and LDL-C (low density lipoprotein cholesterol) were determined by automatic biochemical analyzer. Animals with plasma TC of 9-15 mmol/L were selected as model animals (refer to the following reference for the method of animal modeling: Burrier, R. E., Smith, A. A., Mcgregor, D. G, Hoos, L. M., Zilli, D. L., Davis, H. R. The effect of acyl CoA: cholesterol acyltransferase inhibition on the uptake, esterification and secretion of cholesterol by the hamster small intestine. J. *Pharm. Exp. Ther.*, 1995, 272, 156-163).

2. Compound Screening:

The animals were grouped according to TC and LDL-C levels and weight with 6 animals per group. Ezetimibe was used as positive control. The animals were intragastrically administered at a volume of 5 ml/kg for 1 week. Each animal was anesthetized by ether. After weighing, 0.5 ml blood was taken from orbital vein, anticoagulated with heparin, and centrifuged at 5000 rpm for 10 min. The plasma was collected and plasma TC (total cholesterol) and LDL-C (low density lipoprotein cholesterol) levels were determined by automatic biochemical analyzer to evaluate the efficacy of the compounds.

3. Screening Results

According to the in vivo pharmacodynamic screening test, in which Ezetimibe was used as positive control, the results show that compound I-1 (Z), I-2 (Z), I-3 (Z), I-4 (Z), I-5 (Z), I-6 (Z), I-11 (Z), I-12 (Z), I-13 (Z), I-14 (Z), I-15 (Z), I-16 (Z) and I-17 (Z) have the effect of lowering cholesterol. Particularly, the efficacies of compounds I-1 (Z), I-2 (Z), I-3 (Z), I-4 (Z), I-6 (Z), I-15 (Z) and I-17 (Z) are more similar to the positive control, and I-1 (E) also has certain effect on cholesterol-lowering. The screening results are shown in Table 1-12. As I-1 (Z) has a significant efficacy, further experiments were performed to determine its cholesterol lowering effect (see Table 13).

(1) The effect of the compounds on the blood lipid level of hypercholesterolemia golden hamster model

TABLE 1

Effect of compound I-1 on blood lipid level of hypercholesterolemia golden hamster model (x ± s)

| | | | Biochemical indexes (mmol/L) | | | |
|---|---|---|---|---|---|---|
| | | | Before administration (mmol/L) | | After administration (mmol/L) | |
| Groups | Numbers of animals | dose (mg/kg) | TC | LDL-C | TC | LDL-C |
| Model | 6 | — | 9.93 ± 1.33 | 2.43 ± 0.67 | 12.86 ± 2.49** | 3.18 ± 1.64 |
| Ezetimibe | 6 | 2 | 9.9 ± 1.24 | 2.55 ± 0.96 | 4.21 ± 0.68*** | 0.57 ± 0.34*** |
| I-1(E) | 6 | 10 | 9.85 ± 1.2 | 2.51 ± 0.91 | 8.7 ± 0.93* | 1.74 ± 0.62 |
| I-1(E) | 6 | 2 | 9.84 ± 1.14 | 2.21 ± 0.47 | 11.19 ± 0.69 | 2.21 ± 0.37 |
| I-1(E) | 6 | 0.4 | 9.85 ± 1.1 | 2.44 ± 0.46 | 12.42 ± 1.4 | 2.84 ± 0.59 |
| I-1(Z) | 6 | 10 | 9.76 ± 1 | 2.48 ± 0.67 | 4.3 ± 0.85*** | 0.42 ± 0.2*** |
| I-1(Z) | 6 | 2 | 9.74 ± 0.98 | 2.57 ± 0.47 | 4.9 ± 0.62*** | 0.71 ± 0.49*** |
| I-1(Z) | 6 | 0.4 | 9.74 ± 0.99 | 2.26 ± 0.65 | 6.46 ± 0.58*** | 1.52 ± 0.31* |

Note:
comparing the data before administration with the data after administration,
*$P < 0.05$,
**$P < 0.01$,
***$P < 0.001$.
(*$P < 0.05$ indicates there are significant statistical difference between the treatment groups and the control group; $P < 0.01$, there are very significant statistical difference between the treatment groups and the control group; *$P < 0.001$ indicates there are highly significant statistical difference between the treatment groups and the control group. The same meanings are referred hereinafter.)

TABLE 2

Effect of compound I-1 on lowering the levels of TC and LDL-C

| Groups | Numbers of animals | Dose (mg/kg) | Reducing TC % | Reducing LDL-C % |
|---|---|---|---|---|
| Ezetimibe | 6 | 2 | 57.4 | 77.6 |
| I-1(E) | 6 | 10 | 11.7 | 30.7 |
| I-1(E) | 6 | 2 | −20.9 | 0 |
| I-1(E) | 6 | 0.4 | −26.1 | −16.4 |
| I-1(Z) | 6 | 10 | 55.9 | 83.1 |
| I-1(Z) | 6 | 2 | 49.7 | 72.4 |
| I-1(Z) | 6 | 0.4 | 33.7 | 32.7 |

TABLE 3

Effect of compound I-1 (Z) on blood lipid level of hypercholesterolemia golden hamster model (x ± s)

| Groups | Numbers of animals | Dose (mg/kg) | Biochemical indexes (mmol/L) | | | |
|---|---|---|---|---|---|---|
| | | | Before administration (mmol/L) | | After administration (mmol/L) | |
| | | | TC | LDL | TC | LDL |
| Model | 6 | — | 9.49 ± 0.86 | 1.92 ± 0.74 | 13.63 ± 2.57** | 2.77 ± 0.81* |
| Ezetimibe | 6 | 1 | 9.49 ± 1.14 | 1.81 ± 0.44 | 5.62 ± 0.48*** | 1.16 ± 0.44** |
| I-1(Z) | 6 | 4 | 9.51 ± 1.04 | 1.84 ± 0.18 | 4.37 ± 0.59*** | 0.99 ± 0.28 |
| I-1(Z) | 6 | 1 | 9.49 ± 1.12 | 1.85 ± 0.5 | 5.79 ± 0.99 | 1.19 ± 0.16 |

Note:
comparing the data before administration with the data after administration,
*$P < 0.05$,
**$P < 0.01$,
***$P < 0.001$.

TABLE 4

Effect of compound I-1(Z) on reduction of the levels of TC and LDL-C

| Groups | Numbers of animals | Dose (mg/kg) | Reducing TC % | Reducing LDL % |
|---|---|---|---|---|
| Ezetimibe | 6 | 1 | 58.8 | 36.0 |
| I-1(Z) | 6 | 4 | 67.9 | 46.2 |
| I-1(Z) | 6 | 1 | 57.5 | 35.7 |

TABLE 5

Effect of compound I on blood lipid level of hypercholesterolemia golden hamster model (x ± s)

| Groups | n | Dose (mg/kg) | Biochemical indexes (mmol/L) | | | |
|---|---|---|---|---|---|---|
| | | | Before administration | | After administration | |
| | | | TC | LDL | TC | LDL |
| model | 6 | — | 10.88 ± 1.21 | 4.78 ± 1.25 | 10.53 ± 1.84 | 3.55 ± 1.23 |
| Ezetimibe | 6 | 1 | 10.88 ± 1.15 | 5.41 ± 1.45 | 4.51 ± 0.61*** | 1.3 ± 0.3*** |
| I-12(Z) | 6 | 10 | 10.83 ± 1.11 | 4.82 ± 1.27 | 4.86 ± 0.5*** | 1.34 ± 0.37*** |
| I-12(Z) | 6 | 1 | 10.85 ± 1.02 | 4.33 ± 0.83 | 5.29 ± 0.88*** | 1.58 ± 0.3*** |
| I-13(Z) | 6 | 10 | 10.85 ± 0.97 | 4.19 ± 1.07 | 4.81 ± 0.37*** | 1.27 ± 0.24*** |
| I-13(Z) | 6 | 1 | 10.91 ± 0.99 | 4.82 ± 1.35 | 6.92 ± 1.65*** | 1.98 ± 0.86*** |

Note:
comparing the data before administration with the data after administration,
***$P < 0.001$.

TABLE 6

Effect of compound I on lowering the levels of TC and LDL-C

| Groups | n | Dose (mg/kg) | Reducing TC % | Reducing LDL-C % |
|---|---|---|---|---|
| Ezetimibe | 6 | 1 | 58.3 | 76 |
| I-12(Z) | 6 | 10 | 54.8 | 71.5 |
| I-12(Z) | 6 | 1 | 50.9 | 62.8 |
| I-13(Z) | 6 | 10 | 55.4 | 68.8 |
| I-13(Z) | 6 | 1 | 36.8 | 58.1 |

TABLE 7

Effect of compound I on blood lipid level of hypercholesterolemia golden hamster model (x ± s)

| Groups | n | Dose (mg/kg) | Biochemical indexes (mmol/L) | | | |
|---|---|---|---|---|---|---|
| | | | Before administration | | After administration | |
| | | | TC | LDL | TC | LDL |
| Model | 6 | — | 10.97 ± 1.31 | 4.25 ± 0.8 | 11.66 ± 2.46 | 2.87 ± 0.67 |
| Ezetimibe | 6 | 1 | 10.92 ± 1.25 | 4.54 ± 0.6 | 5.58 ± 0.42*** | 1.62 ± 0.41*** |
| I-14(Z) | 6 | 3 | 10.9 ± 1.21 | 2.74 ± 0.6 | 6.06 ± 2.02*** | 2.01 ± 0.96* |
| I-14(Z) | 6 | 1 | 10.91 ± 1.17 | 4.07 ± 1.72 | 9.34 ± 2.58 | 2.56 ± 0.59 |
| I-15(Z) | 6 | 3 | 10.91 ± 1.13 | 4.86 ± 2.26 | 5.37 ± 1.15*** | 1.44 ± 0.56*** |
| I-15(Z) | 6 | 1 | 10.93 ± 1.1 | 3.8 ± 0.75 | 6.76 ± 1.68*** | 1.99 ± 0.23** |

Note:
comparing the data before administration with the data after administration,
*$P < 0.05$,
**$P < 0.01$,
***$P < 0.001$.

TABLE 8

Effect of compound I on lowering the levels of TC and LDL-C

| Groups | n | Dose (mg/kg) | Reducing TC % | Reducing LDL-C % |
|---|---|---|---|---|
| Ezetimibe | 6 | 1 | 48.1 | 64.2 |
| I-14(Z) | 6 | 3 | 44.4 | 52.3 |
| I-14(Z) | 6 | 1 | 13.5 | 28.6 |
| I-15(Z) | 6 | 3 | 50.8 | 70.4 |
| I-15(Z) | 6 | 1 | 38.1 | 46.5 |

TABLE 9

Effect of compound I on blood lipid level of hypercholesterolemia golden hamster model (x ± s)

| Groups | n | Dose (mg/kg) | Before administration TC | Before administration LDL | After administration TC | After administration LDL |
|---|---|---|---|---|---|---|
| Model | 6 | — | 9.92 ± 0.6 | 2.89 ± 0.72 | 15.34 ± 2.47 | 3.14 ± 0.74 |
| Ezetimibe | 6 | 1 | 9.87 ± 0.92 | 2.77 ± 0.72 | 5.45 ± 0.95*** | 1.0 ± 0.33*** |
| I-6(Z) | 6 | 10 | 9.86 ± 0.97 | 2.83 ± 0.71 | 5.28 ± 1.1*** | 0.93 ± 0.26*** |
| I-6(Z) | 6 | 1 | 9.78 ± 0.82 | 2.76 ± 0.63 | 7.45 ± 1.04*** | 1.57 ± 0.35*** |
| I-5(Z) | 6 | 10 | 9.88 ± 0.93 | 2.73 ± 0.7 | 5.73 ± 0.76*** | 1.0 ± 0.23*** |
| I-5(Z) | 6 | 1 | 9.86 ± 0.68 | 2.84 ± 0.49 | 10.55 ± 1.62*** | 2.18 ± 0.58** |
| I-11(Z) | 6 | 10 | 9.83 ± 1.1 | 2.76 ± 0.54 | 6.11 ± 1.75*** | 1.28 ± 0.47*** |
| I-11(Z) | 6 | 1 | 9.94 ± 1.06 | 2.75 ± 0.55 | 7.98 ± 0.81*** | 1.65 ± 0.57*** |
| I-16(Z) | 6 | 10 | 9.96 ± 0.8 | 2.66 ± 0.62 | 6.0 ± 0.77*** | 1.1 ± 0.39*** |
| I-16(Z) | 6 | 1 | 9.9 ± 0.47 | 2.67 ± 0.39 | 9.61 ± 0.54*** | 2.15 ± 0.39** |

Note:
comparing the data before administration with the data after administration,
**$P < 0.01$,
***$P < 0.001$.

TABLE 10

Effect of compound I on lowering the levels of TC and LDL-C

| Groups | n | Dose (mg/kg) | Reducing TC % | Reducing LDL-C % |
|---|---|---|---|---|
| Ezetimibe | 6 | 1 | 64.4 | 68.2 |
| I-6(Z) | 6 | 10 | 65.6 | 70.4 |
| I-6(Z) | 6 | 1 | 51.5 | 50.2 |
| I-5(Z) | 6 | 10 | 62.7 | 68.1 |
| I-5(Z) | 6 | 1 | 31.2 | 30.7 |
| I-11(Z) | 6 | 10 | 60.2 | 59.2 |
| I-11(Z) | 6 | 1 | 48.0 | 47.7 |
| I-16(Z) | 6 | 10 | 60.9 | 65.0 |
| I-16(Z) | 6 | 1 | 37.4 | 31.7 |

TABLE 11

Effect of compound I on blood lipid level of hypercholesterolemia golden hamster model (x ± s)

| Group | n | Dose (mg/kg) | Before administration TC | Before administration LDL-C | After administration TC | After administration LDL-C |
|---|---|---|---|---|---|---|
| Model | 6 | — | 12.72 ± 1.46 | 2.94 ± 0.86 | 15.33 ± 4.45 | 3.21 ± 2.28 |
| Ezetimibe | 6 | 1 | 12.74 ± 1.44 | 2.88 ± 0.79 | 5.29 ± 0.89*** | 1.13 ± 0.5*** |
| I-2(Z) | 6 | 10 | 12.74 ± 1.32 | 2.76 ± 0.43 | 4.82 ± 0.67*** | 1.01 ± 0.23*** |
| I-3(Z) | 6 | 10 | 12.67 ± 1.35 | 3.38 ± 0.84 | 6.23 ± 1.18*** | 1.14 ± 0.33*** |
| I-4(Z) | 6 | 3 | 12.73 ± 1.27 | 3.25 ± 0.79 | 6.48 ± 0.89*** | 1.51 ± 0.74*** |
| I-17(Z) | 6 | 10 | 12.67 ± 1.28 | 2.98 ± 0.72 | 5.09 ± 1.31*** | 1.19 ± 0.4*** |

Note:
comparing the data before administration with the data after administration,
***$P < 0.001$.

TABLE 12

Effect of compound I on lowering the levels of TC and LDL-C

| Group | n | Dose (mg/kg) | Reducing TC % | Reducing LDL-C % |
|---|---|---|---|---|
| Ezetimibe | 6 | 1 | 58.5 | 60.8 |
| I-2(Z) | 6 | 5 | 62.2 | 63.4 |
| I-3(Z) | 6 | 10 | 50.8 | 66.3 |
| I-4(Z) | 6 | 5 | 49.1 | 53.5 |
| I-17(Z) | 6 | 10 | 59.8 | 60.1 |

(2) The effect of the compounds on the blood lipid level of normal guinea pigs

TABLE 13

Effect of compound I-1(Z) on blood lipid level of normal guinea pig (x ± s)

| Group | Animals (n) | Dose mg/kg | After administration (mmol/L) TG | TC | LDL | HDL |
|---|---|---|---|---|---|---|
| model | 5 | — | 0.42 ± 0.09 | 1.74 ± 0.23 | 1.69 ± 0.29 | 0.43 ± 0.06 |
| Ezetimibe | 6 | 2.5 | 0.41 ± 0.12 | 1.14 ± 0.24* | 0.99 ± 0.28* | 0.41 ± 0.05 |
| I-1(Z) | 5 | 2.5 | 0.31 ± 0.12 | 1.17 ± 0.25* | 0.86 ± 0.29* | 0.47 ± 0.05 |
| I-1(Z) | 6 | 0.5 | 0.44 ± 0.06 | 1.9 ± 0.2 | 1.75 ± 0.29 | 0.4 ± 0.07 |
| I-1(Z) | 6 | 0.1 | 0.38 ± 0.05 | 1.77 ± 0.43 | 1.73 ± 0.48 | 0.47 ± 0.08 |

Note:
comparing the data of the present compounds with the data of the model group,
*$P < 0.05$.

The pharmacodynamic tests show that, compound I-1 (Z), I-2 (Z), I-3 (Z), I-4 (Z), I-5 (Z), I-6 (Z), I-11 (Z), I-12 (Z), I-13 (Z), I-14 (Z), I-15 (Z), I-16 (Z) and I-17 (Z) can significantly reduce the plasma TC and LDL-C levels of the golden hamster hypercholesterolemic model, all of which have significant statistical difference. In particular, the effects of compound I-2 (Z), I-3 (Z), I-4 (Z), I-6 (Z), I-15 (Z), I-17 (Z) are similar to that of the positive control, i.e. Ezetimibe, at the same dose, and the effect of compound I-1 (Z) is the same as that of the positive control at the same dose. Compound I-1 (E) can also lower plasma TC and LDL-C levels of the animals, but it reduces less than 50% of the amount reduced by Ezetimibe and I-1 (Z). In addition, compound I-1 (Z) can significantly reduce the plasma TC and LDL-C levels of normal guinea pigs and the effect is the same as that of the positive control, i.e. Ezetimibe, at the same dose.

The invention claimed is:

1. A compound represented by formula (I)

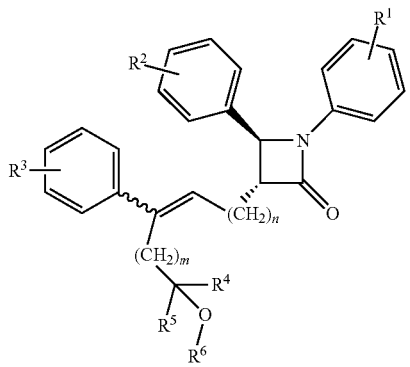

Formula (I)

or a pharmaceutically acceptable salt thereof, wherein:
$R^1$ is 1 to 3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, hydroxyl, $C_1$-$C_6$ alkoxy, benzyloxy and —OCOR$^7$;
$R^2$ is 1 to 3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, hydroxyl, $C_1$-$C_6$ alkoxy, $C_6$-$C_{10}$ aryloxy, ($C_6$-$C_{10}$ aryl) methoxy and —OCOR$^7$;
$R^3$ is 1-3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, $C_1$-$C_6$ alkoxy and benzyloxy;
$R^4$ is selected from the group consisting of hydrogen, $C_1$-$C_6$ alkyl, $C_2$-$C_6$ alkenyl and $C_3$-$C_6$ cycloalkyl;
$R^5$ is selected from the group consisting of hydrogen, $C_1$-$C_6$ alkyl, $C_2$-$C_6$ alkenyl and $C_3$-$C_6$ cycloalkyl;
$R^6$ is hydrogen or —COR$^7$;
$R^7$ is $C_1$-$C_{10}$ alkyl, phenyl or phenyl substituted with at least one substituent selected from the group consisting of halogen, trifluoromethyl, cyano, hydroxyl, $C_1$-$C_6$ alkyl, $C_2$-$C_6$ alkenyl, $C_3$-$C_6$ cycloalkyl, $C_1$-$C_6$ alkoxy, phenoxy and benzyloxy;
m is 0, 1, 2 or 3; and
n is 1, 2 or 3.

2. The compound according to claim 1, wherein $R^1$ is 1-3 substituents independently selected from the group consisting of halogen.

3. The compound according to claim 2, wherein $R^1$ is 1-3 substituents independently selected from the group consisting of fluorine and chlorine.

4. The compound according to claim 1, wherein $R^2$ is 1-3 substituents independently selected from the group consisting of hydroxyl, $C_1$-$C_6$ alkoxy and —OCOR$^7$, wherein $R^7$ is selected from the group consisting of $C_1$-$C_{10}$ alkyl, phenyl or phenyl substituted by at least one substituent selected from the group consisting of halogen, trifluoromethyl, cyano, hydroxyl, $C_1$-$C_6$ alkyl, $C_2$-$C_6$ alkenyl, $C_3$-$C_6$ cycloalkyl, $C_1$-$C_6$ alkoxy and benzyloxy.

5. The compound according to claim 1, wherein $R^2$ is 1-3 substituents independently selected from the group consisting of hydroxyl, methoxy, phenyloxy and —OCOR$^7$.

6. The compound according to claim 1, wherein $R^3$ is 1-3 substituents independently selected from the group consisting of halogen.

7. The compound according to claim 6, wherein $R^3$ is 1-3 substituents independently selected from the group consisting of fluorine and chlorine.

8. The compound according to claim 1, wherein $R^4$ is hydrogen or $C_1$-$C_6$ alkyl.

9. The compound according to claim 8, wherein $R^4$ is hydrogen or methyl.

10. The compound according to claim 1, wherein $R^5$ is hydrogen or $C_1$-$C_6$ alkyl.

11. The compound according to claim 10, wherein $R^5$ is hydrogen or methyl.

12. The compound according to claim 1, wherein $R^6$ is hydrogen.

13. The compound according to claim 1, wherein $R^6$ is —COR$^7$, wherein $R^7$ is $C_1$-$C_{10}$ alkyl, phenyl or phenyl substituted by at least one substituent selected from the group consisting of halogen, trifluoromethyl, cyano, hydroxyl, $C_1$-$C_6$ alkyl, $C_2$-$C_6$ alkenyl, $C_3$-$C_6$ cycloalkyl, $C_1$-$C_6$ alkoxy, phenoxy and benzyloxy.

14. The compound according to claim 1, wherein $R^7$ is $C_1$-$C_{10}$ alkyl.

15. The compound according to claim 1, wherein m is 0 or 1.

16. The compound according to claim 1, wherein n is 1.

17. The compound according to claim 1 selected from the group consisting of:
(3R,4S)-1-(4-fluorophenyl)-3-[(Z)-3-(4-fluorophenyl)-4-hydroxy-but-2-enyl]-4-(4-hydroxyphenyl)azetidin-2-one (I-1 Z configuration)
(3R,4S)-1-(4-fluorophenyl)-3-[(E)-3-(4-fluorophenyl)-4-hydroxy-but-2-enyl]-4-(4-hydroxyphenyl)azetidin-2-one (I-1 E configuration)
(3R,4S)-1-(4-fluorophenyl)-3-[(Z)-3-(4-fluorophenyl)-4-hydroxy-but-2-enyl]-4-(4-methoxyphenyl)azetidin-2-one (I-2 Z configuration)
(3R,4S)-1-(4-fluorophenyl)-3-[(E)-3-(4-fluorophenyl)-4-hydroxy-but-2-enyl]-4-(4-methoxyphenyl)azetidin-2-one (I-2 E configuration)
(3R,4S)-1-(4-fluorophenyl)-3-[(Z)-3-(4-fluorophenyl)-4-hydroxy-but-2-enyl]-4-(4-phenoxyphenyl)azetidin-2-one (I-3 Z configuration)
(3R,4S)-1-(4-fluorophenyl)-3-[(E)-3-(4-fluorophenyl)-4-hydroxy-but-2-enyl]-4-(4-phenoxyphenyl)azetidin-2-one (I-3 E configuration)
(3R,4S)-4-(4-benzyloxyphenyl)-1-(4-fluorophenyl)-3-[(Z)-3-(4-fluorophenyl)-4-hydroxy-but-2-enyl]azetidin-2-one (I-4 Z configuration)
(3R,4S)-4-(4-benzyloxyphenyl)-1-(4-fluorophenyl)-3-[(E)-3-(4-fluorophenyl)-4-hydroxy-but-2-enyl]azetidin-2-one (I-4 E configuration)
(3R,4S)-4-(4-benzoyloxyphenyl)-1-(4-fluorophenyl)-3-[(Z)-3-(4-fluorophenyl)-4-hydroxy-but-2-enyl]azetidin-2-one (I-5 Z configuration)
(3R,4S)-4-(4-acetoxyphenyl)-1-(4-fluorophenyl)-3-[(Z)-3-(4-fluorophenyl)-4-hydroxy-but-2-enyl]azetidin-2-one (I-6 Z configuration)

(3R,4S)-4-(4-benzoyloxyphenyl)-1-(4-fluorophenyl)-3-[(Z)-3-(4-fluorophenyl)-4-hydroxy-pent-2-enyl]azetidin-2-one (I-7 Z configuration)

(3R,4S)-1-(4-fluorophenyl)-3-[(Z)-3-(4-fluorophenyl)-4-hydroxy-pent-2-enyl]-4-(4-hydroxyphenyl)azetidin-2-one (I-8 Z configuration)

(3R,4S)-1-(4-fluorophenyl)-3-[(E)-3-(4-fluorophenyl)-4-hydroxy-pent-2-enyl]-4-(4-hydroxyphenyl)azetidin-2-one (I-8 E configuration)

(3R,4S)-4-(4-benzoyloxyphenyl)-1-(4-fluorophenyl)-3-[(Z)-3-(4-fluorophenyl)-4-hydroxy-4-methyl-pent-2-enyl]azetidin-2-one (I-9 Z configuration)

(3R,4S)-1-(4-fluorophenyl)-3-[(Z)-3-(4-fluorophenyl)-4-hydroxy-4-methyl-pent-2-enyl]-4-(4-hydroxyphenyl)azetidin-2-one (I-10 Z configuration)

(3R,4S)-3-[(Z)-4-acetoxy-3-(4-fluorophenyl)-but-2-enyl]-4-(4-acetoxyphenyl)-1-(4-fluorophenyl)azetidin-2-one (I-11 Z configuration)

(3R,4S)-3-[(Z)-4-acetoxy-3-(4-fluorophenyl)-but-2-enyl]-1-(4-fluorophenyl)-4-(4-hydroxyphenyl)azetidin-2-one (I-12 Z configuration)

(3R,4S)-3-[(Z)-4-benzoyloxy-3-(4-fluorophenyl)-but-2-enyl]-1-(4-fluorophenyl)-4-(4-hydroxyphenyl)azetidin-2-one (I-13 Z configuration)

(3R,4S)-3-[(Z)-4-(4-fluorobenzoyloxy)-3-(4-fluorophenyl)-but-2-enyl]-1-(4-fluorophenyl)-4-(4-hydroxyphenyl)azetidin-2-one (I-14 Z configuration)

(3R,4S)-1-(4-fluorophenyl)-3-[(Z)-3-(4-fluorophenyl)-4-(4-methylbenzoyloxy)-but-2-enyl]-4-(4-hydroxyphenyl)azetidin-2-one (I-15 Z configuration)

(3R,4S)-3-[(Z)-4-acetoxy-3-(4-fluorophenyl)-but-2-enyl]-4-(4-benzoyloxyphenyl)-1-(4-fluorophenyl)azetidin-2-one (I-16 Z configuration)

(3R,4S)-3-[(Z)-4-acetoxy-3-(4-fluorophenyl)-but-2-enyl]-1-(4-fluorophenyl)-4-(4-methoxyphenyl)azetidin-2-one (I-17 Z configuration); and (3R,4S)-3-[(E)-4-acetoxy-3-(4-fluorophenyl)-but-2-enyl]-1-(4-fluorophenyl)-4-(4-methoxyphenyl)azetidin-2-one (I-17 E configuration).

18. A process for preparing the compound represented by formula I, comprising deprotection of a compound represented by formula V under basic conditions,

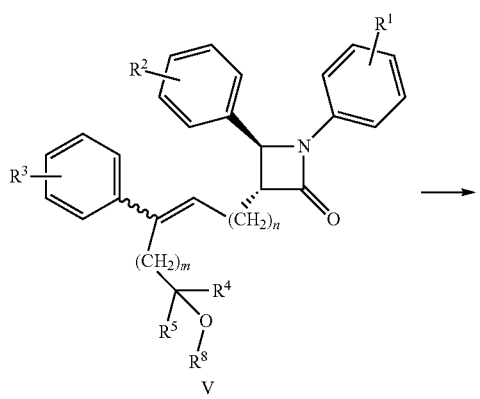

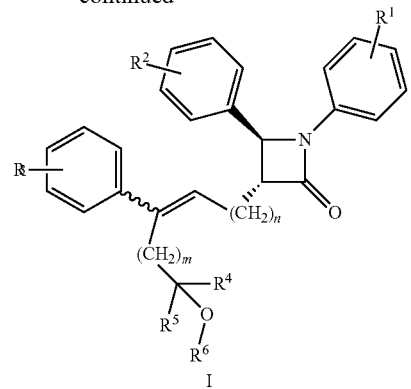

wherein $R^1$ is 1 to 3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, hydroxyl, $C_1$-$C_6$ alkoxy, benzyloxy and —$OCOR^7$;

$R^2$ is 1 to 3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, hydroxyl, $C_1$-$C_6$ alkoxy, $C_6$-$C_{10}$ aryloxy, ($C_6$-$C_{10}$ aryl) methoxy and —$OCOR^7$;

$R^3$ is 1-3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, $C_1$-$C_6$ alkoxy and benzyloxy;

$R^4$ is selected from the group consisting of hydrogen, $C_1$-$C_6$ alkyl, $C_2$-$C_6$ alkenyl and $C_3$-$C_6$ cycloalkyl;

$R^5$ is selected from the group consisting of hydrogen, $C_1$-$C_6$ alkyl, $C_2$-$C_6$ alkenyl and $C_3$-$C_6$ cycloalkyl;

$R^6$ is hydrogen or —$COR^7$;

$R^7$ is $C_1$-$C_{10}$ alkyl, phenyl or phenyl substituted with at least one substituent selected from the group consisting of halogen, trifluoromethyl, cyano, hydroxyl, $C_1$-$C_6$ alkyl, $C_2$-$C_6$ alkenyl, $C_3$-$C_6$ cycloalkyl, $C_1$-$C_6$ alkoxy, phenoxy and benzyloxy;

m is 0, 1, 2 or 3;

n is 1, 2 or 3; and wherein $R^8$ is a hydroxyl protection group.

19. A pharmaceutical composition comprising an effective amount of the compound represented by formula (I) or the pharmaceutically acceptable salt thereof.

20. A method for preparing a compound of formula V, comprising treatment of a compound represented by formula IV with N, O-bis(trimethylsilyl)acetamide and subsequent cyclization of the resultant silylated product,

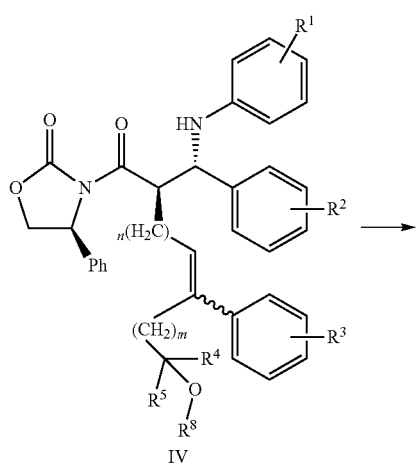

IV

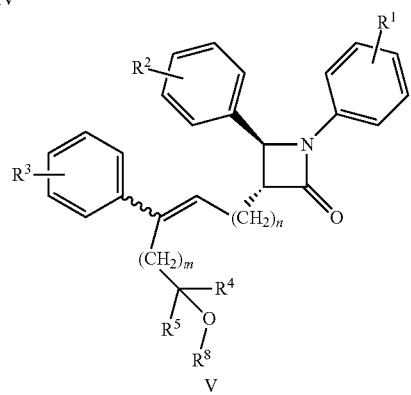

V wherein,

R$^1$ is 1 to 3 substituents independently selected from the group consisting of hydrogen, halogen, trifluoromethyl, cyano, C$_1$-C$_6$ alkyl, C$_2$-C$_6$ alkenyl, C$_3$-C$_6$ cycloalkyl, hydroxyl, C$_1$-C$_6$ alkoxy, benzyloxy and —OCOR$^7$;

R$^2$ is 1 to 3 substituents independently selected from the group consisting of hydrogen, halogen, trifluoromethyl, cyano, C$_1$-C$_6$ alkyl, C$_2$-C$_6$ alkenyl, C$_3$-C$_6$ cycloalkyl, hydroxyl, C$_1$-C$_6$ alkoxy, C$_6$-C$_{10}$aryloxy, (C$_6$-C$_{10}$ aryl) methoxy and —OCOR$^7$;

R$^3$ is 1-3 substituents independently selected from the group consisting of hydrogen, halogen, trifluoromethyl, cyano, C$_1$-C$_6$ alkyl, C$_2$-C$_6$ alkenyl, C$_3$-C$_6$ cycloalkyl, C$_1$-C$_6$ alkoxy and benzyloxy;

R$^4$ is selected from the group consisting of hydrogen, C$_1$-C$_6$ alkyl, C$_2$-C$_6$ alkenyl and C$_3$-C$_6$ cycloalkyl;

R$^5$ is selected from the group consisting of hydrogen, C$_1$-C$_6$ alkyl, C$_2$-C$_6$ alkenyl and C$_3$-C$_6$ cycloalkyl;

m is 0, 1, 2 or 3;

n is 1, 2 or 3;

R$^7$ is C$_1$-C$_{10}$ alkyl, phenyl or phenyl substituted with at least one substituent selected from the group consisting of halogen, trifluoromethyl, cyano, hydroxyl, C$_1$-C$_6$ alkyl, C$_2$-C$_6$ alkenyl, C$_3$-C$_6$ cycloalkyl, C$_1$-C$_6$ alkoxy, phenoxy and benzyloxy; and wherein R$^8$ is a hydroxyl protection group.

21. A compound represented by formula V,

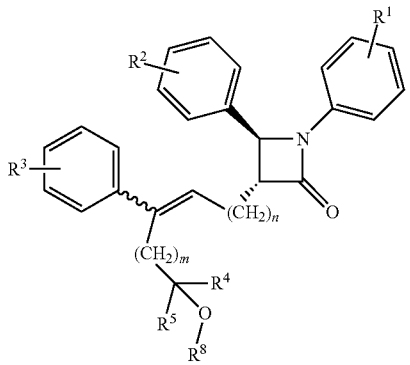

V wherein,

R$^1$ is 1 to 3 substituents independently selected from the group consisting of hydrogen, halogen, trifluoromethyl, cyano, C$_1$-C$_6$ alkyl, C$_2$-C$_6$ alkenyl, C$_3$-C$_6$ cycloalkyl, hydroxyl, C$_1$-C$_6$ alkoxy, benzyloxy and —OCOR$^7$;

R$^2$ is 1 to 3 substituents independently selected from the group consisting of hydrogen, halogen, trifluoromethyl, cyano, C$_1$-C$_6$ alkyl, C$_2$-C$_6$ alkenyl, C$_3$-C$_6$ cycloalkyl, hydroxyl, C$_1$-C$_6$ alkoxy, C$_6$-C$_{10}$ aryloxy, (C$_6$-C$_{10}$ aryl) methoxy and —OCOR$^7$;

R$^3$ is 1-3 substituents independently selected from the group consisting of hydrogen, halogen, trifluoromethyl, cyano, C$_1$-C$_6$ alkyl, C$_2$-C$_6$ alkenyl, C$_3$-C$_6$ cycloalkyl, C$_1$-C$_6$ alkoxy and benzyloxy;

R$^4$ is selected from the group consisting of hydrogen, C$_1$-C$_6$ alkyl, C$_2$-C$_6$ alkenyl and C$_3$-C$_6$ cycloalkyl;

R$^5$ is selected from the group consisting of hydrogen, C$_1$-C$_6$ alkyl, C$_2$-C$_6$ alkenyl and C$_3$-C$_6$ cycloalkyl;

m is 0, 1, 2 or 3;

n is 1, 2 or 3;

R$^7$ is C$_1$-C$_{10}$ alkyl, phenyl or phenyl substituted with at least one substituent selected from the group consisting of halogen, trifluoromethyl, cyano, hydroxyl, C$_1$-C$_6$ alkyl, C$_2$-C$_6$ alkenyl, C$_3$-C$_6$ cycloalkyl, C$_1$-C$_6$ alkoxy, phenoxy and benzyloxy; and wherein R$^8$ is a hydroxyl protection group.

22. A compound represented by formula IV,

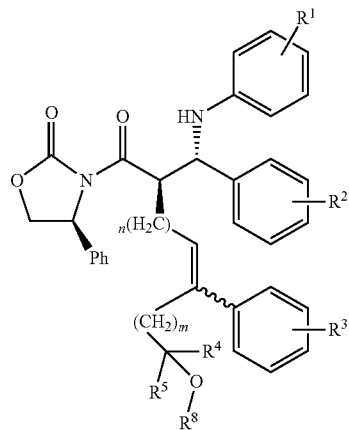

IV wherein,

R$^1$ is 1 to 3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, hydroxyl, $C_1$-$C_6$ alkoxy, benzyloxy and —$OCOR^7$;

$R^2$ is 1 to 3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, hydroxyl, $C_1$-$C_6$ alkoxy, $C_6$-$C_{10}$ aryloxy, ($C_6$-$C_{10}$ aryl) methoxy and —$OCOR^7$;

$R^3$ is 1-3 substituents independently selected from the group consisting of hydrogen, halogen, trifluoromethyl, cyano, $C_1$-$C_6$ alkyl, $C_2$-$C_6$ alkenyl, $C_3$-$C_6$ cycloalkyl, $C_1$-$C_6$ alkoxy and benzyloxy;

$R^4$ is selected from the group consisting of hydrogen, $C_1$-$C_6$ alkyl, $C_2$-$C_6$ alkenyl and $C_3$-$C_6$ cycloalkyl;

$R^5$ is selected from the group consisting of hydrogen, $C_1$-$C_6$ alkyl, $C_2$-$C_6$ alkenyl and $C_3$-$C_6$ cycloalkyl;

m is 0, 1, 2 or 3;

n is 1, 2 or 3;

$R^7$ is $C_1$-$C_{10}$ alkyl, phenyl or phenyl substituted with at least one substituent selected from the group consisting of halogen, trifluoromethyl, cyano, hydroxyl, $C_1$-$C_6$ alkyl, $C_2$-$C_6$ alkenyl, $C_3$-$C_6$ cycloalkyl, $C_1$-$C_6$ alkoxy, phenoxy and benzyloxy; and wherein $R^8$ is a hydroxyl protection group.

23. The compound according to claim 3, wherein $R^1$ is fluorine.

24. The compound according to claim 7, wherein $R^3$ is fluorine.

25. The process according to claim 18, wherein $R^8$ is selected from the group consisting of acetyl, tert-butyldimethylsilyl (TBDMS), trimethylsilyl (TMS), and tert-butyldiphenylsilyl (TBDPS) groups.

26. A method of treating atherosclerosis or lowering plasma cholesterol levels comprising administering an effective amount of the compound of claim 1.

* * * * *